(12) United States Patent
Yazawa et al.

(10) Patent No.: US 7,157,050 B2
(45) Date of Patent: Jan. 2, 2007

(54) SYSTEM AND METHOD FOR DETECTING BIOLOGICAL AND CHEMICAL MATERIAL

(75) Inventors: Yoshiaki Yazawa, Nishitokyo (JP); Masao Kamahori, Kokubunji (JP); Hideki Kambara, Hachiouji (JP); Mitsuo Usami, Tachikawa (JP); Ken Takei, Kawasaki (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/445,038

(22) Filed: May 27, 2003

(65) Prior Publication Data

US 2004/0121354 A1 Jun. 24, 2004

(30) Foreign Application Priority Data

Sep. 6, 2002 (JP) .............................. 2002-260769

(51) Int. Cl.
*G01N 15/06* (2006.01)

(52) U.S. Cl. .................... 422/68.1; 422/61; 435/7.1; 435/7.92; 435/287.1; 435/288.7; 436/524; 455/92; 455/151.2; 340/5.5; 340/5.61; 370/312

(58) Field of Classification Search ................ 422/92, 422/151.2, 61, 68.1, 99; 435/6, 7.1, 287.2, 435/287.9, 973, 7.92, 287.1, 287.7, 288.7; 436/501, 149, 524, 528, 532; 455/92, 151.2; 340/5.5, 5.61; 370/310.2, 312, 359; 700/48; 704/232

See application file for complete search history.

(56) References Cited

U.S. PATENT DOCUMENTS

| | | | | |
|---|---|---|---|---|
| 4,777,019 A | * | 10/1988 | Dandekar | ................. 422/82.02 |
| 5,120,421 A | * | 6/1992 | Glass et al. | .................. 204/406 |
| 5,641,634 A | * | 6/1997 | Mandecki | ...................... 435/6 |
| 5,795,774 A | * | 8/1998 | Matsumoto et al. | ... 204/403.11 |
| 5,871,918 A | * | 2/1999 | Thorp et al. | .................... 435/6 |
| 5,981,166 A | | 11/1999 | Mandecki | ...................... 435/4 |
| 6,051,377 A | | 4/2000 | Mandecki | ...................... 436/6 |
| 6,117,643 A | * | 9/2000 | Simpson et al. | ............ 435/7.1 |
| 6,485,905 B1 | * | 11/2002 | Hefti | ............................. 435/6 |

(Continued)

FOREIGN PATENT DOCUMENTS

WO   WO 97/12030   9/1996

(Continued)

OTHER PUBLICATIONS

Victor Lyamichev, Mary Ann D. Brow, James E. Dahlberg, "Structure-Specific Endonucleolytic Cleaavage of Mucleic Acids by Eubacterial DNA Polymerases", SCIENCE, vol. 260, May 7, 1993, pp. 778-783.

(Continued)

*Primary Examiner*—Long V. Le
*Assistant Examiner*—Leon Y. Lum
(74) *Attorney, Agent, or Firm*—Reed Smith LLP; Stanley P. Fisher, Esq.; Juan Carlos A. Marquez, Esq.

(57) ABSTRACT

A system and method are provided for detecting biological and chemical material. To measure biological materials such as genes easily at low costs, the device for implementing a small-sized, high sensitive, economical measurement apparatus is provided. Probes appropriate for target biological materials are fixed on a chip, on which a sensor, identification number, and radio communication function are implemented, the captured targets are detected by the sensors, and the result of sensing are transferred to an external control unit by the radio communication function. The small-sized, high sensitivity measurement apparatus for detecting biological and chemical materials such as genes and measuring physical and chemical amounts such as temperature, pressure, pH, and the like can be implemented.

17 Claims, 22 Drawing Sheets

U.S. PATENT DOCUMENTS

| | | | |
|---|---|---|---|
| 6,587,617 B1 * | 7/2003 | Ho | 385/25 |
| 6,649,356 B1 * | 11/2003 | Bryan et al. | 435/7.1 |
| 6,756,223 B1 * | 6/2004 | Roberts et al. | 435/287.2 |
| 2002/0155477 A1 | 10/2002 | Ito | 435/6 |

FOREIGN PATENT DOCUMENTS

| | | |
|---|---|---|
| WO | WO 98/01758 | 6/1997 |

OTHER PUBLICATIONS

Timothy Morris, Betty Robertson, and Margaret Gallagher, "Rapid Reverse Transcription-PCR Detection of Hepatitis C Viris RNA in Serum by Using the TaqMan Fluorogenic Detection System", Journal of Clinical Microbiology, vol. 34, No. 12, Dec. 1996, pp. 2933-2936.

K. Bult et al, "Low Power Systems for Wireless Microsensors", International Symposium on Low Power Electronics and Design, Digest of Technical Papers, 1996, pp. 17-22.

G. Asada, M. Dong, T.S. Lin, F. Newberg, G. Pottie, W.J. Kaiser, "Wireless Integrated Network Sensors: Low Power Systems on a Chip", Proceedings of the European Solid-State Circuits Conference, 1998, pp. 9-16.

Qiuting Huang and Michael Oberle, "A 0.5-mW Passive Telemetry IC for Biomedical Applications", IEEE Journal of Solid-State Circuits, vol. 33, No. 7, Jul. 1998, pp. 937-945.

P.A. Neukomm, I. Roncoroni, D. Nanz and H.H. Quick, "Passive E-field Telemetry: A New Wireless Transmission Principle in Minimally Invasive Medicine", 15th International Symposium in Biotelemetry, pp. 609-617.

E. Souteyrand, J.P. Cloaree, J. R. Martin, C. Wilson, I. Lawrence, S. Mikkelson, and M.F. Lawrence, "Direct Detection of the Hybridization of Synthetic Homo-Oligomer DNA Sequences by Field Effect", J. Phys. Chem. B, 1997, p. 2980-2985.

Peter Van Gerwen et al., "Nanoscaled Interdigitated Electrode Arrays For Biochemical Sensors", Elsevier Science S.A., 1998, pp. 73-79.

Koji Hashimoto, Keiko Ito, and Yoshio Ishimori, "Sequence-Specific Gene Detection with a Gold Electrode Modified with DNA Probes and an Electrochemically Active Dye", Analytical Chemistry, vol. 66, No. 21, Nov. 1, 1994, pp. 3830-3833.

Hidetoshi Arakawa, Masako Maeda, and Akio Tsuji, "Chemiluminescence Enzyme Immunoassay of Cortisol Using Peroxide as Label", Analytical Biochemistry 97, 1979, pp. 248-254.

K. Puget, A. M. Michelson, and S. Avrameas, "Light Emission Techniques for the Microestimation of Femtogram Levels of Peroxidase", Analytical Biochemistry 79, 1977, pp. 447-456.

Thomas Olsson, Gustaf Brunius, Hans Erik Carlsoon, and Anders Thore, "Luminescence Immunoassay (LIA): A Solid-Phase Immunoassay Monitored By Chemiluminescence", Journal of Immunological Methods 25, 1979, pp. 127-135.

Mostafa Ronaghi, Mathias Uhlen, and Pal Nyren, "A Sequencing Method Based on Real-Time Pyrophosphate", Science, vol. 281, Jul. 17, 1998, pp. 363, 365-369.

Patrick O. Brown and Leland Hartwell, "Genomics and human Disease-Variations on Variation", Nature Genetics, vol. 18, Feb. 1998, pp. 91-93.

Hans-Jürgen Hentschel, "Light and Illumination", Japan Scientific Industrial Publishing Society, newly revised 4th edition, 1994, pp. 21-35, with Statement of Relevancy.

Ausubel et al, "Short Protocols in Molecular Biology", John Wiley & Sons, Inc., Third Edition, 1995, pp. 411-415.

* cited by examiner

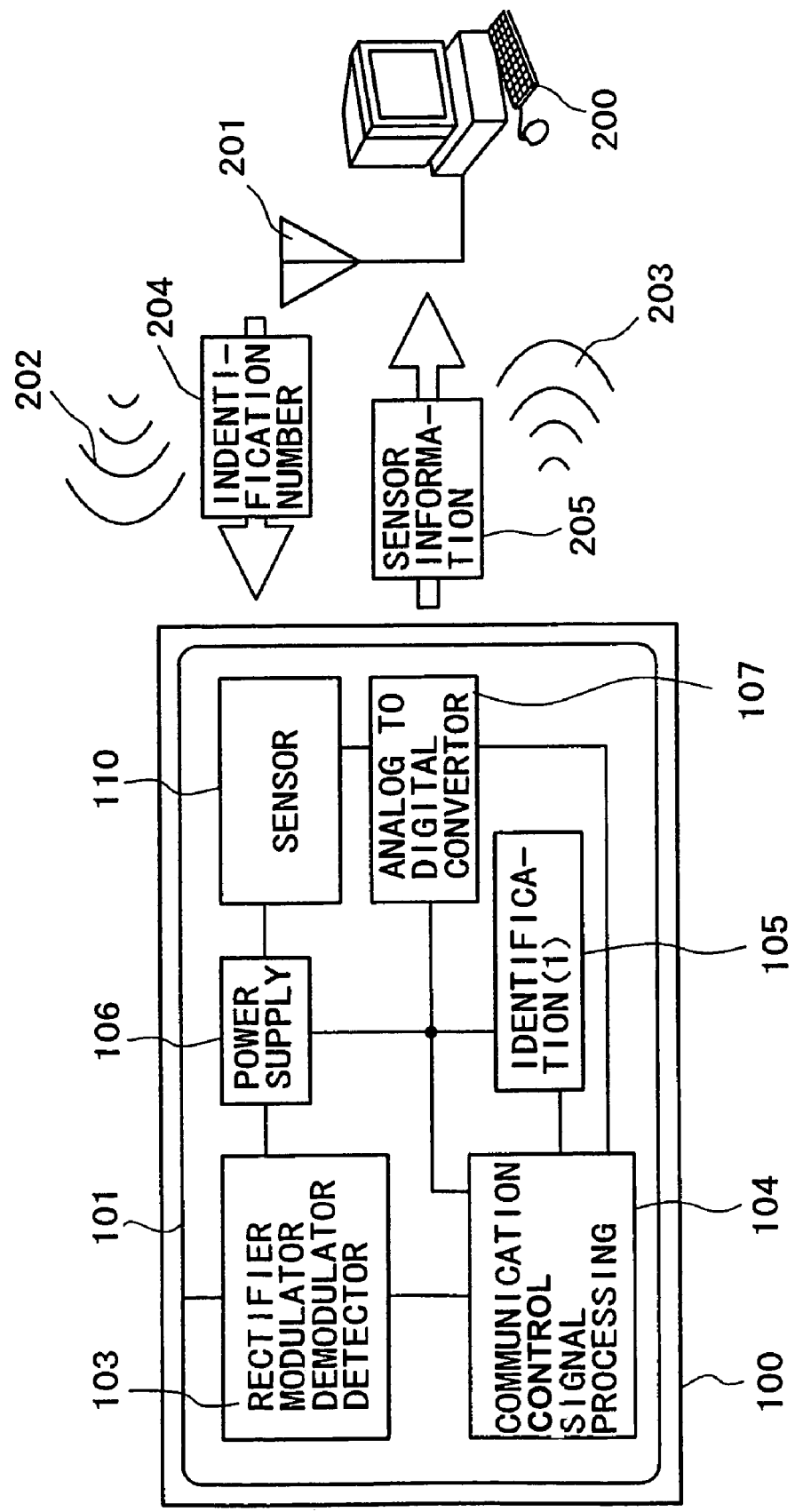

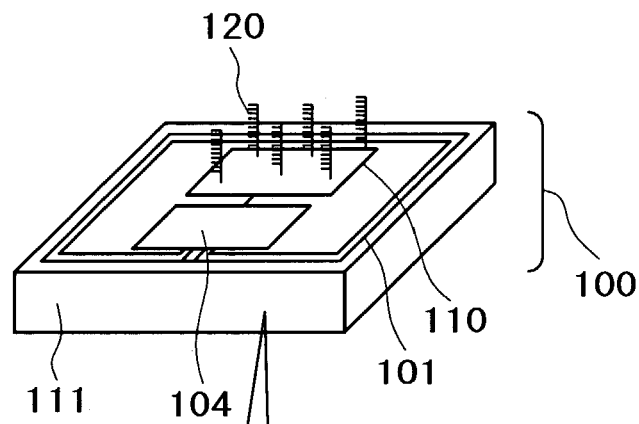
FIG. 4A
FIG. 4B
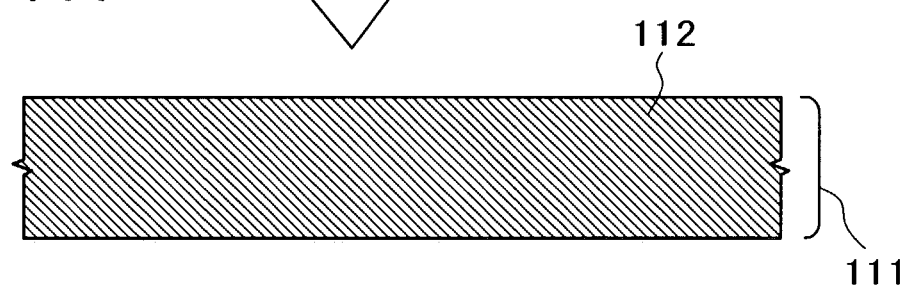
FIG. 4C
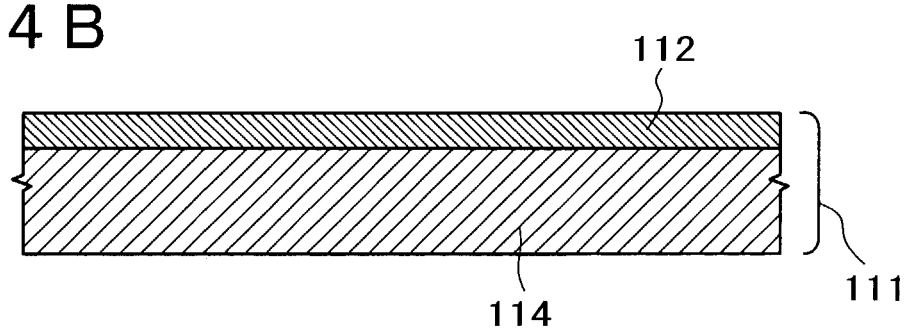

⇩ ANTIGEN-ANTIBODY REACTION

⇩ CHEMILUMINESCENCE

F I G. 1 4
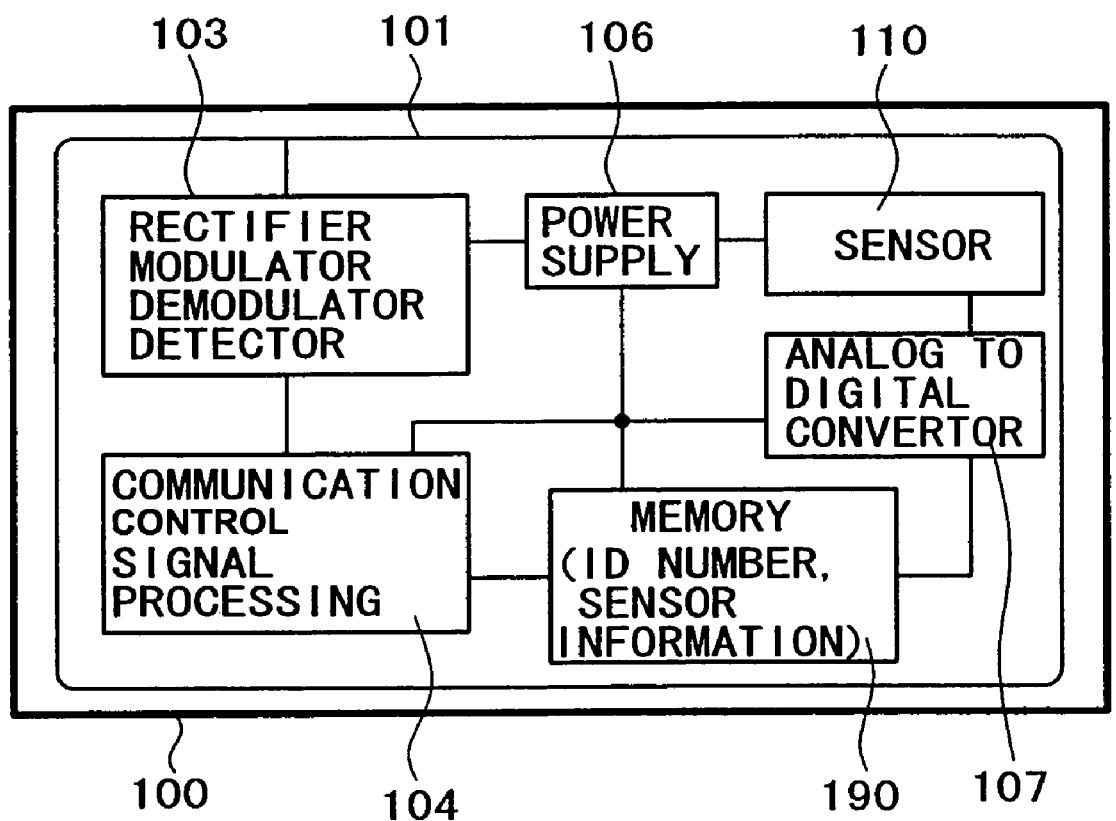

F I G. 1 6 A
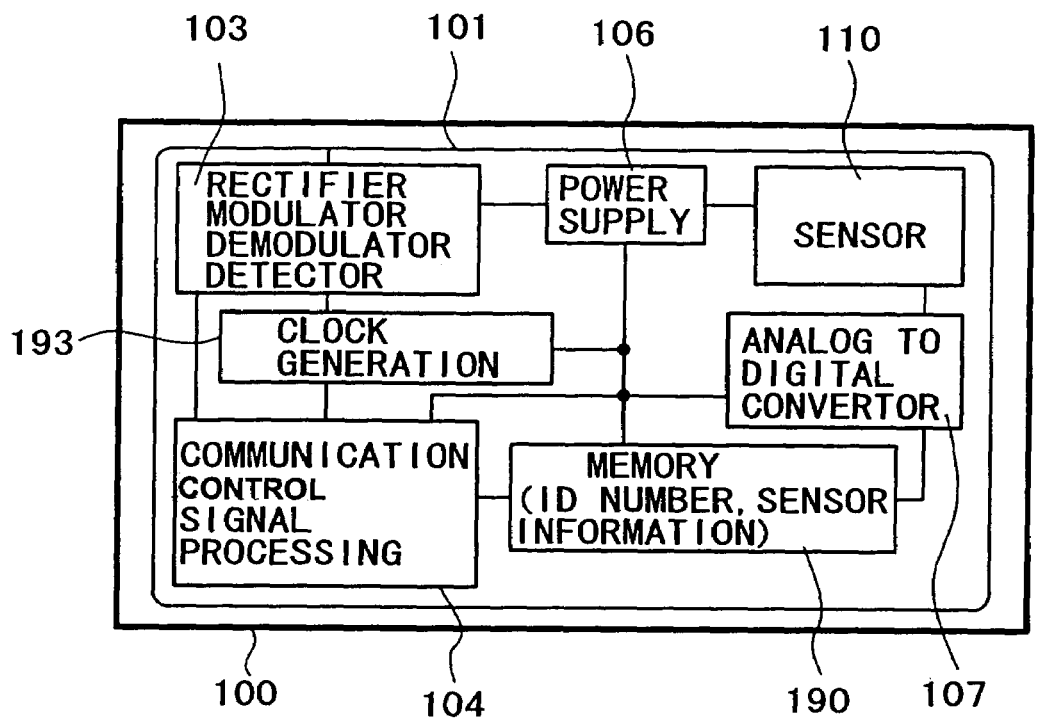
F I G. 1 6 B
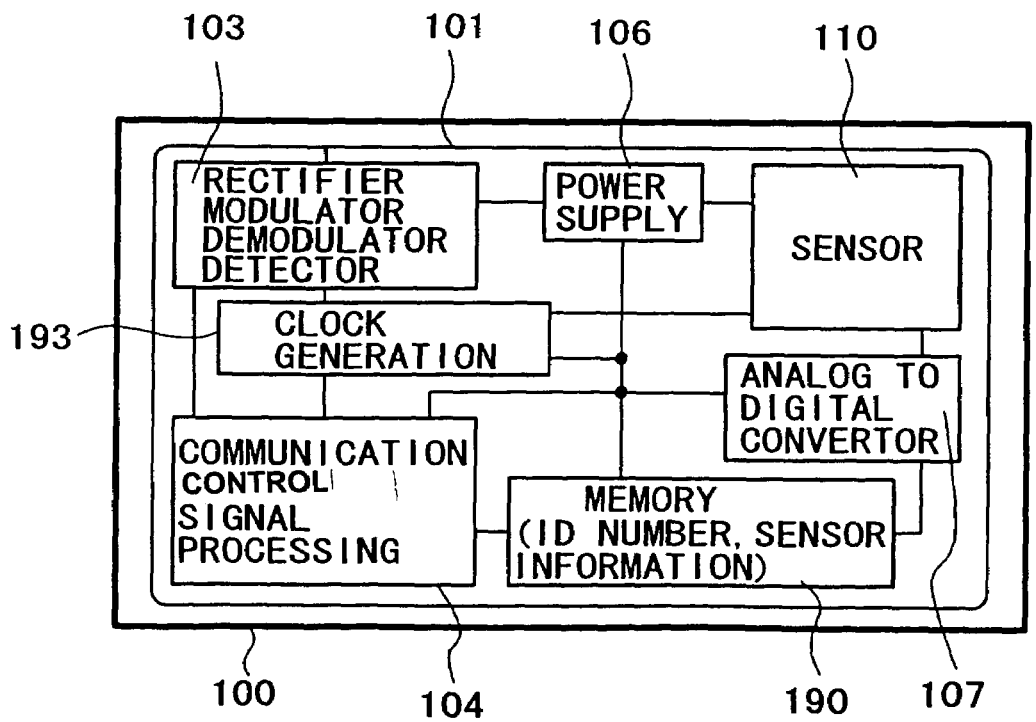

FIG. 17

| NO | FABRICATION PROCESS | CROSS SECTION |
|---|---|---|
| 1 | Si WAFER | |
| 2 | ISOLATION | |
| 3 | EMITTER DIFFUSION FOR PHOTODIODE | |
| 4 | GATE OXIDE MOS Vth CONTROL | |
| 5 | POLY Si DEPOSITION MOS GATE FORMATION | |
| 6 | MOS DRAIN AND SOURCE | |
| 7 | 1st METALLIZATION | |
| 8 | 2nd, 3rd METALLIZATION AND PASSIVATION | PHOTODIODE  n-CHANNEL MOS  p-CHANNEL MOS |
| 9 | PAD | |

F I G. 1 8
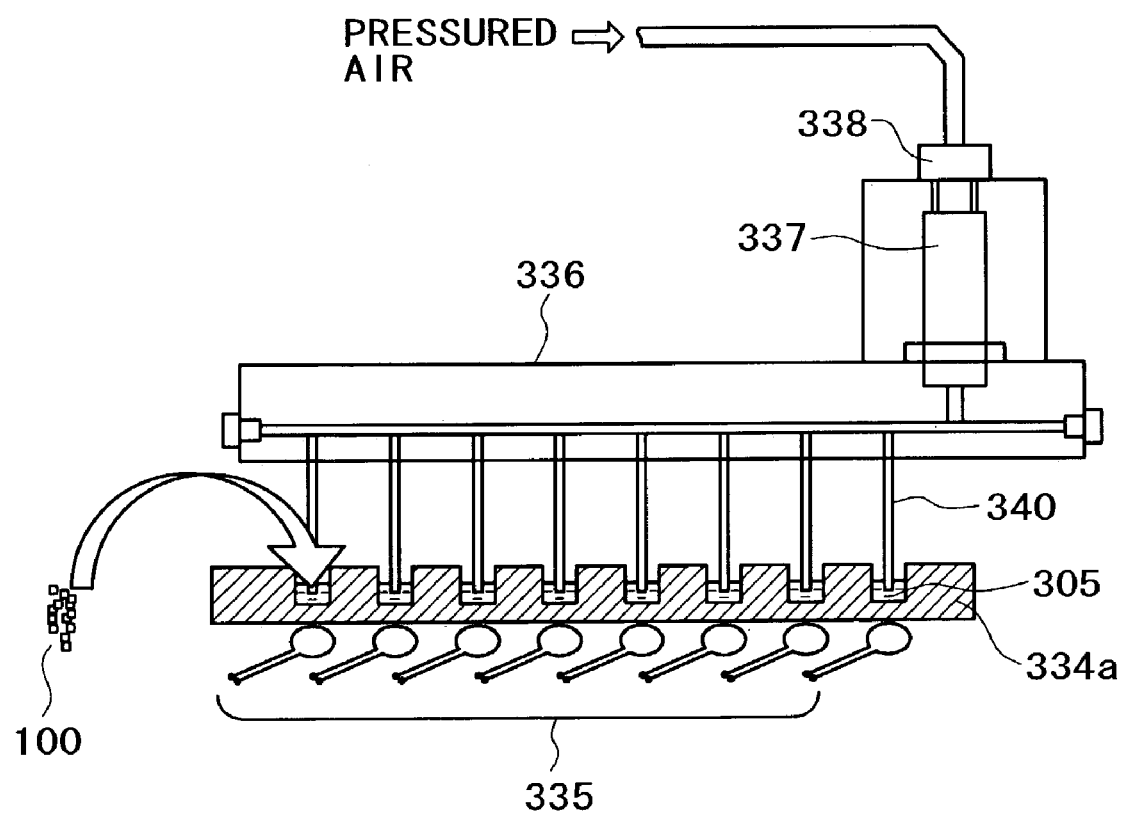

SYSTEM AND METHOD FOR DETECTING BIOLOGICAL AND CHEMICAL MATERIAL

BACKGROUND OF THE INVENTION

1. Field of the Invention

The present invention generally relates to detecting biological and chemical material and, more particularly, to systems and methods of hybridizing nucleic acid in experiments in order to analyze a DNA sequence, and to detect biological materials such as proteins and ATPs.

2. Discussion of Background

As the end of human genome sequence research approaches, increasingly more attempts have been made to make full use of gene information in the medical arena. As post genome-sequence researches, gene expression analysis and analysis of single nucleotide polymorphisms (SNPs) in genes attract special attention. To elucidate the casual relationship between the functions of genes or genes themselves and diseases or drug sensitivity, the genes expressing under various conditions and gene mutation in the individuals are studied. Now, this accumulated knowledge of genes is used to diagnose diseases.

In diagnosing diseases, typing of the known genes or the presence of their mutation is involved unlike searching for unknown genes. It is preferable that it may be performed at a low cost and to do so, various types of methods have been developed. In the future, a wide range of tests from diagnosing diseases based on single genes to diagnosing diseases developing due to the synergy effect between various genes and the environmental conditions and testing plural genes for identifying drug sensitivity will attract special attention. In this case, it is desirable that many kinds of genes can be tested concurrently instead of individual genes or gene mutation. The system, which enables SNPs to be tested including the process for amplifying the target site of the gene at a low cost, is being sought. The systems applicable to SNP analysis or genetic testing include Invader assay (Science 260, 778 (1993)), Taqman assay (J. Clin. Microbio 1.34, 2933 (1996)), DNA microarray (Nature Gent. 18, 91 (1998), and pyrosequencing (Science 281, 363 (1998)). Among others, the DNA microarray, which allows many sites to be tested, attracts attention as a future gene sequencing technique.

In the microarray technique, various types of oligo DNAs or cDNAs are spotted on slide glass plates coated with poly-L-lysine. Spotting is performed using a device called spotter (or, arrayer), which can form spots with a diameter of several tens to 200 μm at an interval of 100 to 500 μm. The spotted oligo DNAs or cDNAs are post-processed, dried in the room, and stored. A target sample is prepared by extracting RNAs from a sample cell and preparing cDNAs marked with any of fluorescent dyes such as Cyanine3 and Cyanine5. The target sample solution is dropped on the microarray and incubated in a moisture chamber at 65° C. for about 10 hours. After hybridization ends, the microarray is washed with a 0.1% SDS solution and dried at room temperature. To evaluate the microarray, a scanner is used. An argon ion laser, for example, is used for an exiting light source and a photomultiplier tube, for example, is used for a luminescent detector. Any influence of a background irradiated from any other points than a focal point is eliminated using a confocal optics, improving an S/N ratio. To evaluate fluorescence at many spots, the microarray needs to be aligned with a reading optics at a high accuracy. For this reason, the scanner has an x-y stage, which can move within an error of 10 μm or less.

The method for implementing low-cost measurement by integrating and miniaturizing the sensor and radio communication parts has been proposed (Bult, K., et al.,: Proceedings of International Symposium on Low Power Electronics and Design, IEEE (1996), p 17–22, or Asada, G., et al.,: Proceedings of the European Solid-State Circuit Conference ESSCIRC'98 p 9–16). The method for supplying the power required by the integrated sensor and signal processing circuit using RF (radio frequency) (Huang, Q., Oberle, M.,: IEEE Journal of Solid-State Circuits vol. 33 (1998) p 937–946 or Neukomm, P., Rencoroni, I. and Quick, H.,: $15^{th}$ International Symposium in Biotelemetry (1999) p 609–617) or infrared ray (U.S. Pat. No. 5,981,166) has also been proposed. In these conventional examples, one sensor chip is generally installed for each target to be measured such as a single sample or in the apparatus intended to measure one test term. In addition, in these examples, the information on the result of-detection by the sensor is sent by the radio communication part but no description of information communication for identifying the target to be measured is found. In this device the sensor can not be installed for each of plural identified targets to be measured or in the apparatus for measuring plural terms to be tested.

The method for using microparticles to determine the presence and concentration of biological molecules has also been disclosed (U.S. Pat. No. 6,051,377). In this method, index numbers are assigned to individual particles. The presence and concentration of biological molecules are detected using fluorescence, luminescence, or radiation while index numbers are decoded independently.

To implement the measurement system for biological and chemical samples, which is widely applicable to genetic and protein testing in the medical arena, foods, environmental measurement systems, process control in the chemical plants, and the like, it is required that: (1) the measurement system is small-sized, (2) many items can be tested in a single reaction cell, (3) the, test requires a shorter time, (4) not only biological materials such as nucleic acid and proteins, but also temperature, pressure, pH, and ion concentration can be identified, and (5) a small amount of sample is sufficient for testing.

The microarray is the slide glass plate, on which probe DNAs with diameters of several tens to several hundreds μm have been spotted. To form the spots, the device called a spotter drops a solution containing various probes on the slide glass plate. To ensure that a small amount of sample can be reacted with many probes, the spots must be formed at a high density, and the spots mentioned above are arranged at an interval of several tens to several hundreds μm. For this reason, it is desirable that the spotter has performance, which can form the spots at a high accuracy of position with an error of 10 μm or less. Since spotted amounts and shapes of solution may lead to any variation in measured value for fluorescent intensity during evaluation, the spotter must has performance, which can form the spots at a high uniformity. It has been eagerly sought that the measurement device, which allows the probes to be fixed uniformly and the desired various probes to be easily selected for measurement, avoiding this problem, is developed.

With respect to the device for detecting signals, fluorescent detection is used for the microarray as mentioned above. In this case, a laser as an exciting light source, a confocal optics, a photomultiplier tube, and a high accuracy x and y movable stage are required. Accordingly, it is difficult that the microarray is miniaturized and manufactured at a low cost and an economical and easy detection device has been sought. The microarray is a useful technique in that many items can be tested concurrently while generally, the reaction rate of target DNA hybridization with the probes fixed on the substrate is slow requiring about ten hours in some cases and it is difficult to improve its throughput. For this reason, it has been sought that an easy and speedy testing method is developed.

To not only measure biological materials such as nucleic acid and proteins but also measure physically and chemically temperature, pressure, and ion concentration, a lead line is required to output sensor signals. Measurement of many items, in particular, requires excess space and cost in lead line wiring, line connection, and signal processing. The advent of the measurement system, in which no lead line is required because the detection and measurement parts are not in contact with one another, and which enables many items to be easily tested has been expected. Such a technique is also necessary that the measurement apparatus with a sensor for sensing biological or chemical materials mentioned above and the sensor for measuring physical and chemical amounts are put together in the same reaction cell for concurrent measurement.

Moreover, in prior art disclosed in U.S. Pat. No. 6,051,377, the detection of captured biological molecules on the microparticles takes time because individual particles are detected and requires the mechanisms for detecting biological molecules and index numbers. To overcome this problem, the measurement system, in which the same mechanism can detect the captured biological molecules on the microparticles and index numbers, has been desired.

SUMMARY OF THE INVENTION

Broadly speaking, the present invention fills these needs by providing a system and method for detecting biological and chemical material. It should be appreciated that the present invention can be implemented in numerous ways, including as a process, an apparatus, a system, a device or a method. Several inventive embodiments of the present invention are described below.

A measurement system is provided, which has a reaction cell for containing a measurement apparatus and an external control unit, the measurement apparatus having one kind of probes and sensors, an information communication device, and a information storage device for storing carrier-recognition information, the external control unit sends and receives information to and from the information communication device of the measurement apparatus in no contact with one another.

A measurement system is provided, which has a reaction cell containing plural measurement apparatuses and an external control unit, the measurement apparatuses having one kind of probes and sensors, an information communication device, and an information storage device for storing carrier-recognition information, the information communication device causing the carrier-recognition information to be identified by the external control unit and sending the information on detection of specific coupling in the probe by the sensor to the external control unit as electrical signals.

A measurement kit is provided, which comprises a measurement apparatus, a sensor mounted on the measurement apparatus, a receiving mechanism mounted on the measurement apparatus for receiving information supplied externally, a sending mechanism mounted on the measurement apparatus for sending information detected by the sensor, and a device mounted on the measurement apparatus for storing information containing carrier recognition information detected by the sensor, wherein the measurement apparatus is surface-modified to fix one kind of probe.

Specifically, in the devices mentioned above, the measurement apparatus is used, in which the probe appropriate for the target to be tested is fixed and the sensor for detecting the target captured by the probe, the circuit blocks providing the functions for processing sensor information, controlling communication with the external control unit, containing and matching identification numbers, and generating and controlling power, and an antenna for communication with the external control unit are incorporated.

The measurement apparatus is put into the reaction cell containing the sample solution to detect the presence or the amount of the target captured by the probe fixed on the measurement apparatus and convert detection information signals into the digital electrical signals. On the other hand, the external control unit sends the recognition number by device of an electromagnetic wave, a change in the magnetic field, or a change in the electric field so that the specific measurement apparatus can be identified among plural measurement apparatuses. Any of an electromagnetic wave, changes in the magnetic field, and changes in the electric field is transmitted to the plural measurement apparatuses in the sample vessel, received by the antenna formed on the measurement apparatus, and after passing through the verifier and the demodulator, matched against the measurement apparatus-specific identification numbers pre-written in the measurement apparatuses. Matching is performed in the matching circuit for each measurement apparatus. When the identification number sent from the external control unit is matched against the pre-written identification number and match is established between them, the measured signals are transmitted from the measurement apparatus, in which match is achieved, through the communication control/signal processing circuit block and modulation circuit block via the antenna to the external control unit by device of an electromagnetic wave sent externally, a change in the magnetic field, or a change in the electric field for reading in. The power consumed by the control circuit block and the sensor is supplied from the DC power source comprising rectifying and smoothing circuits in the control block and a voltage regulator when an electromagnetic wave, a change in the magnetic field, or a change in the electric field is received via the antenna.

As the probes fixed in the measurement apparatuses, DNAs, proteins, peptides, low-molecular weight compounds are used. Alternately, the sensor, which directly measures temperature, pressure, and ion concentration without using probes, may be used. When the probes are used, the sensor signal for measuring the degree of target coupling must be converted into electric signals in the measurement apparatus. For this reason, when probes are used for sensing, the sensor is used, which provides probe-target coupling to be read as any electric signal such as FET channel conductivity, electrode-electrode impedance, oxidation-reduction current, and photoelectric current. For the sensor, which monitors the physical and chemical amounts such as the temperature, pressure, pH, and the like of the sample solution, the same sensor signal processing device as that for DNA sensing can be used after the result of the target sensed is converted into an electric signal. Accordingly, the measurement apparatuses with a common external control unit and an antenna, which are put in the reaction cell, can be easily designed, manufactured, and supplied to measure various items. Thus, the user can build the measurement system, which can measure a satisfactory number of items to be tested, by selecting the appropriate measurement apparatus for the target to be tested.

According to our invention, simple and small-sized measurement apparatus is provided. Our invention enables the apparatus to shorten the measuring time and to measure using small amount of the sample. The probes are immobilized homogeneously, and selected easily for the measurement. Furthermore, the recognition information for measurement apparatus and the detection information obtained by the sensor included in the apparatus are transferred to an external control unit wirelessly.

The invention encompasses other embodiments of a method, an apparatus, and a computer-readable medium, which are configured as set forth above and with other features and alternatives.

BRIEF DESCRIPTION OF THE DRAWINGS

The present invention will be readily understood by the following detailed description in conjunction with the accompanying drawings. To facilitate this description, like reference numerals designate like structural elements.

FIG. 1B is a view showing a function block in a chemical sample measurement system using a biological and chemical sample measurement apparatus according to embodiment 1 of the present invention;

FIG. 4A is a view showing the structure of a substrate for a measurement apparatuses, on which a function block is assembled together according to the embodiment 4 of the present invention;

FIG. 4B is a view showing the insulative substrate 114 such as glass, quartz, and ceramics, on which a thin silicon film are applied;

Figure 5A:
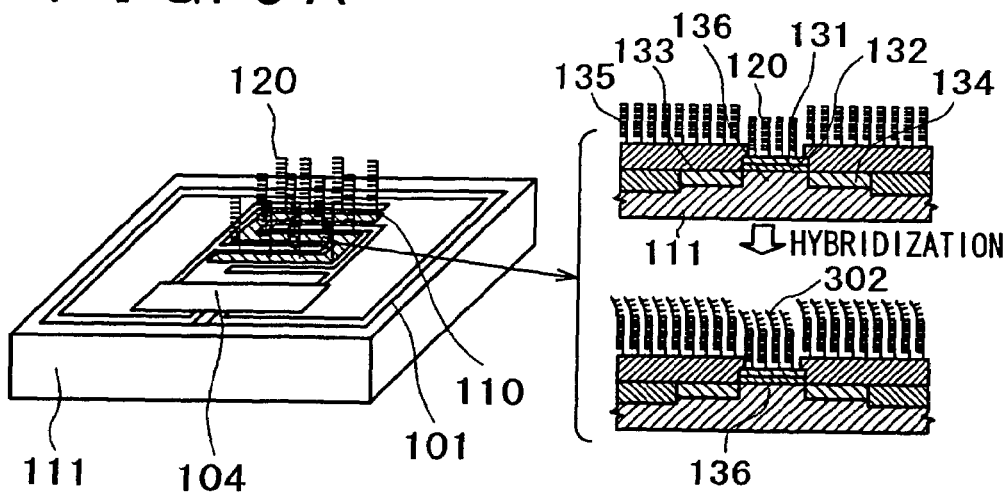
Figure 5B:
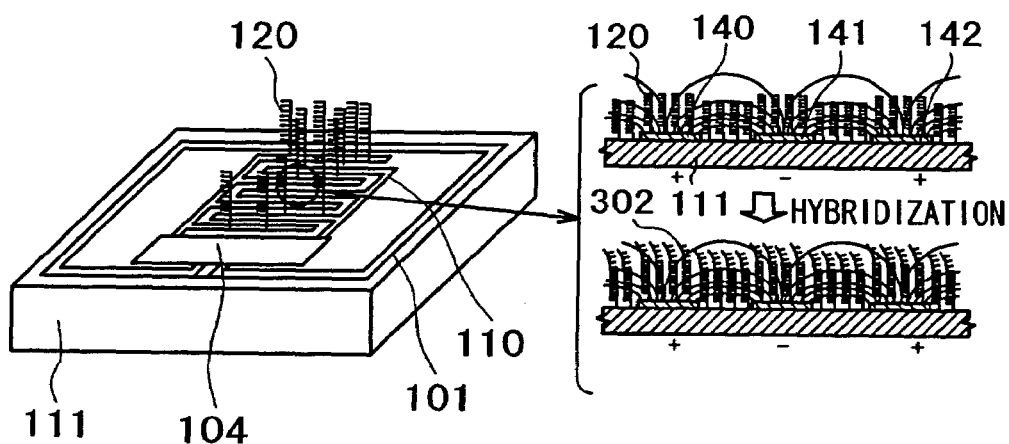
Figure 5C:
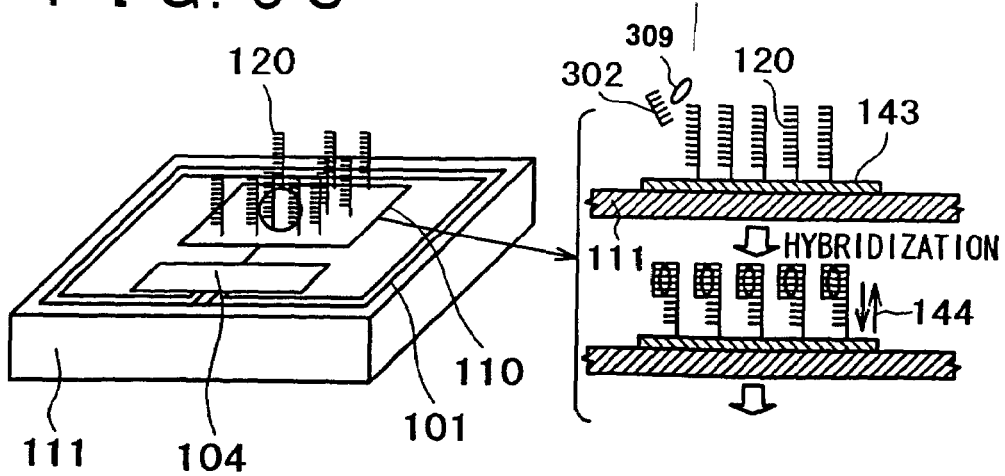
Figure 6A:
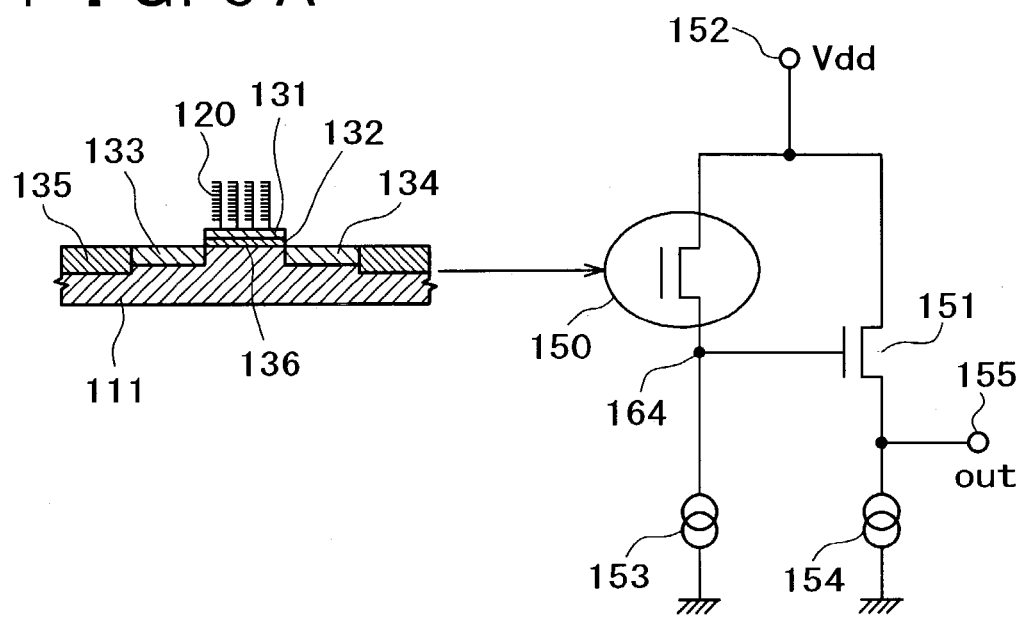
Figure 6B:
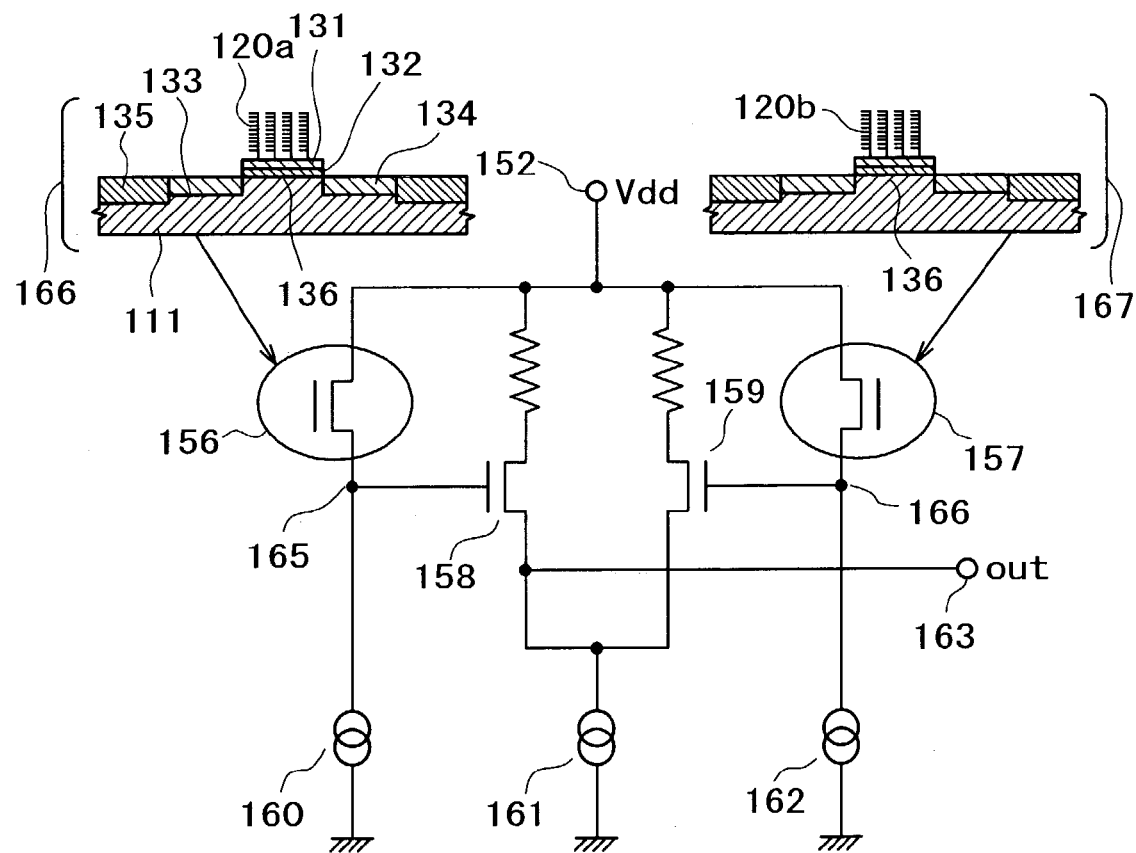
Figure 7A:
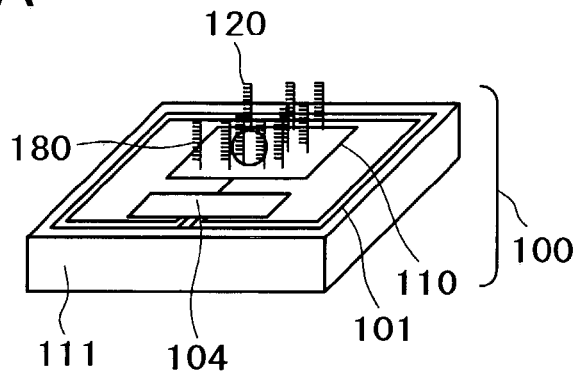
Figure 7B:
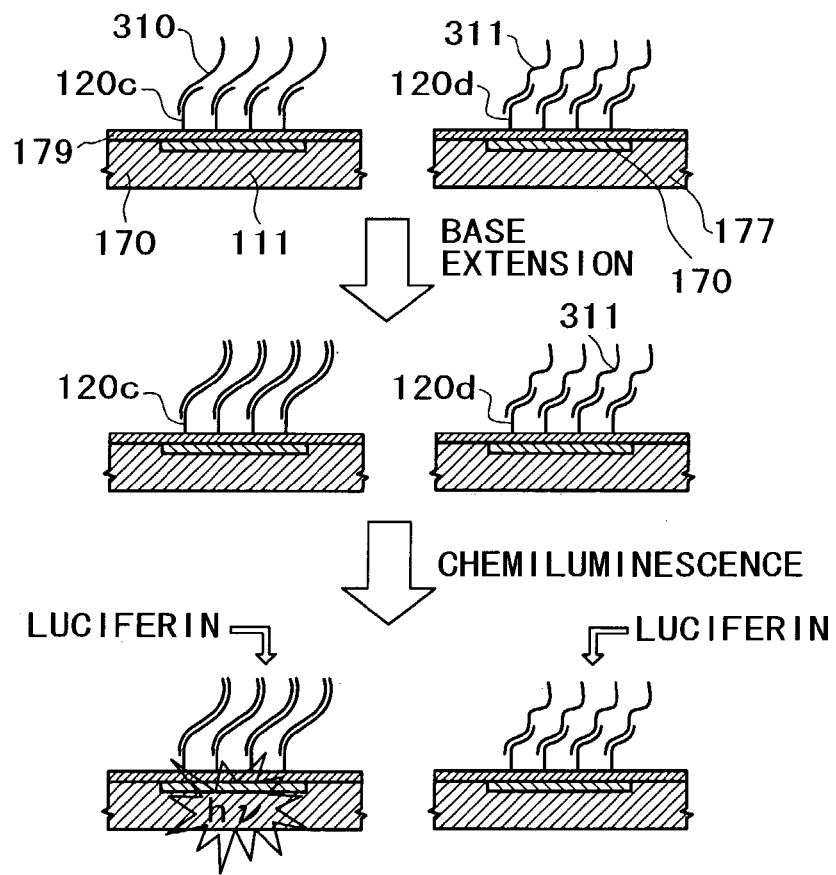
Figure 7C:
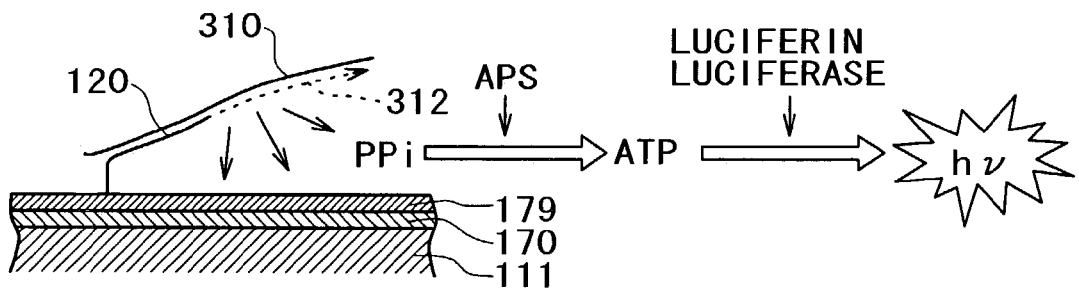
Figure 8A:
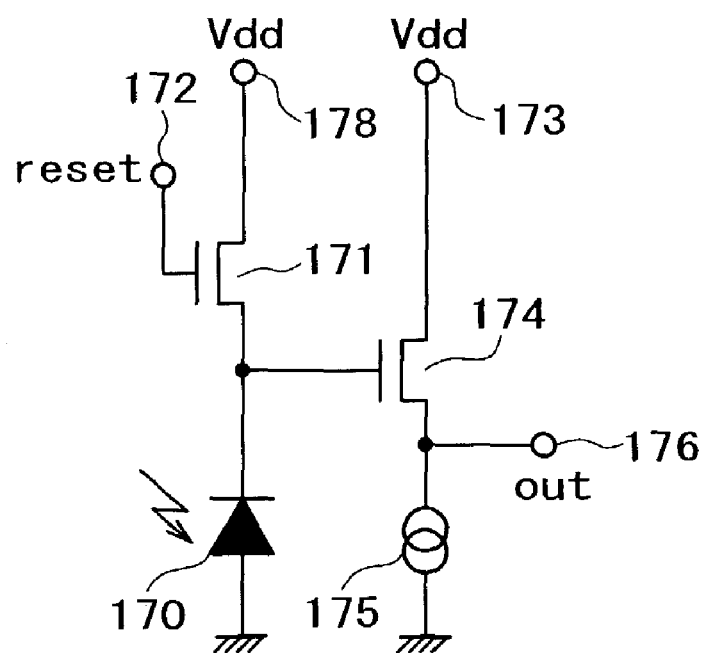
Figure 8B:
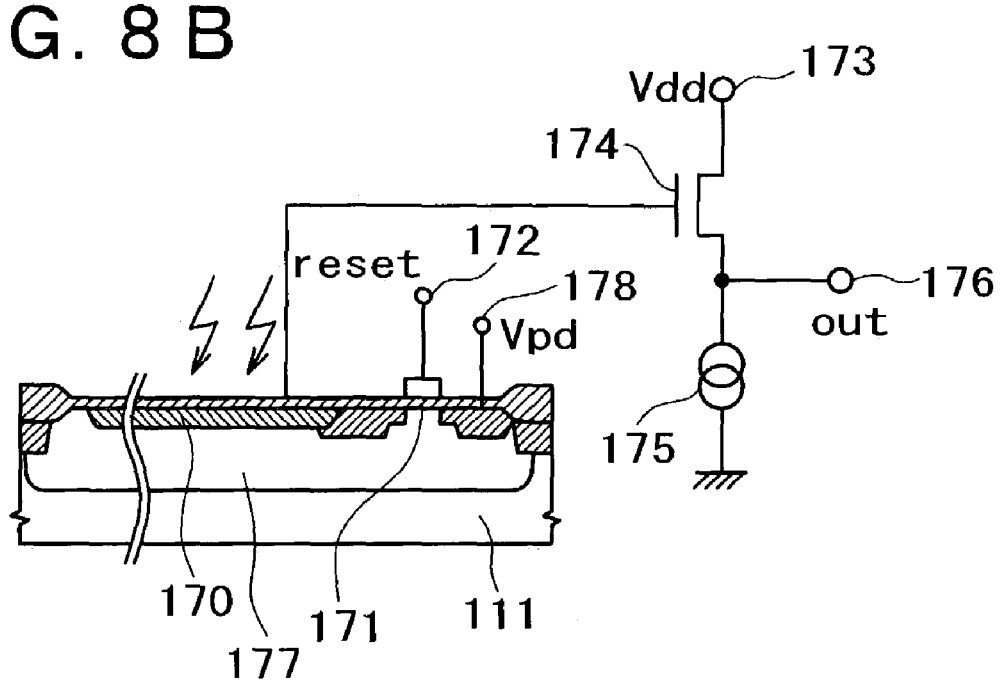
Figure 9A:
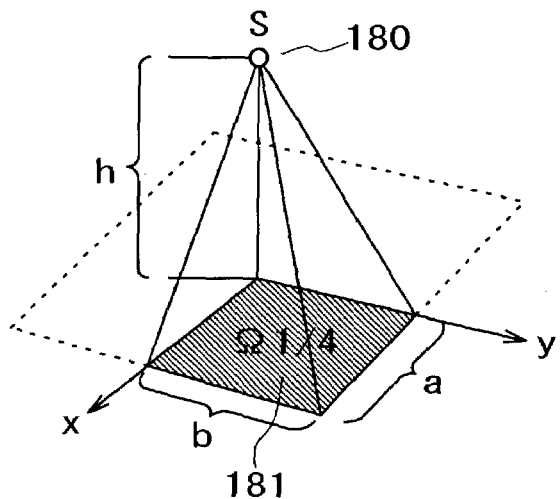
Figure 9B:
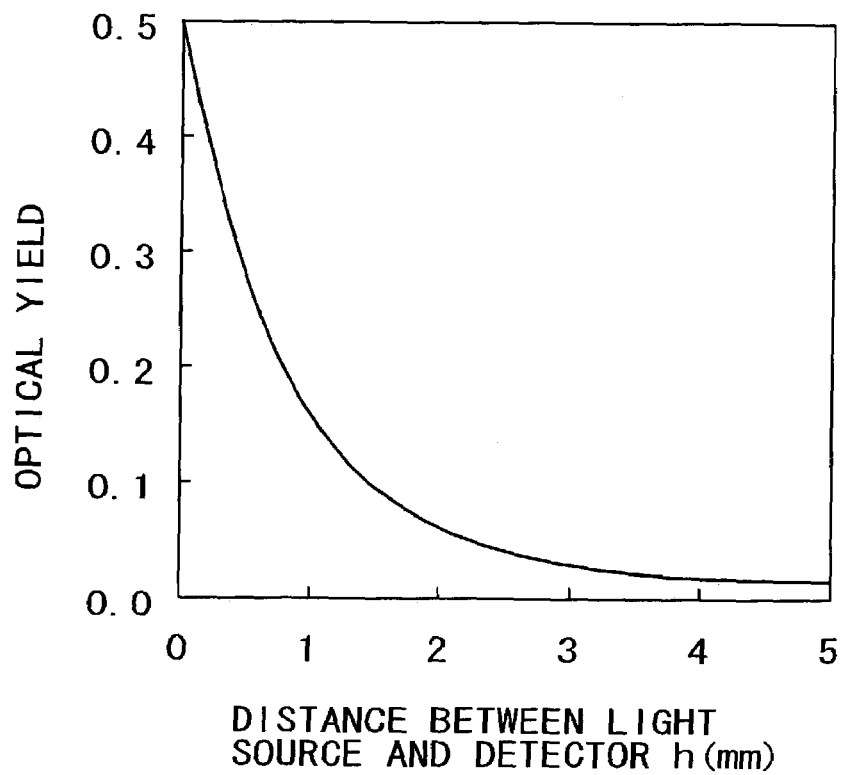
Figure 10A:
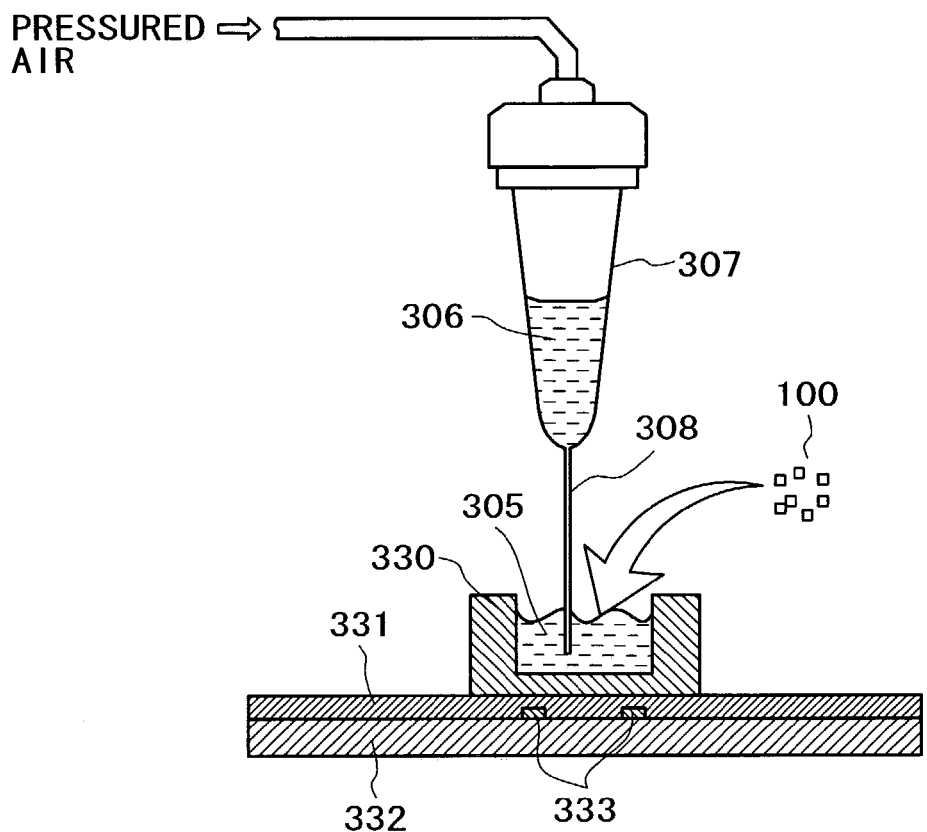
Figure 10B:
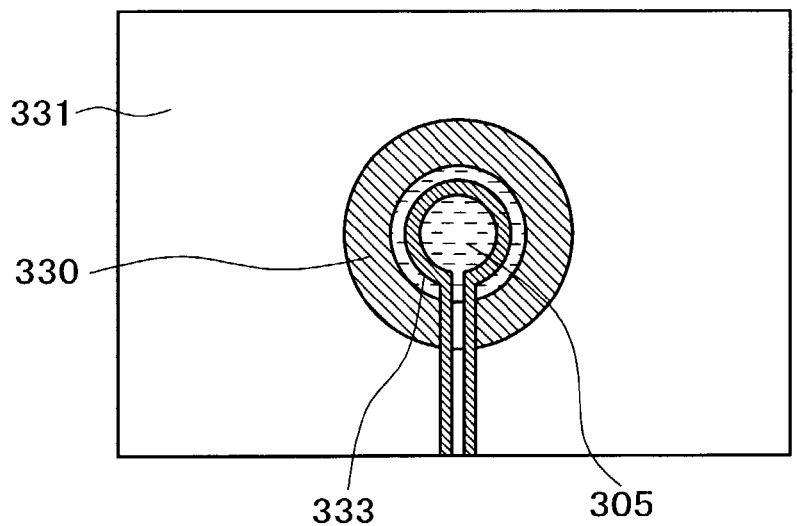
Figure 11:
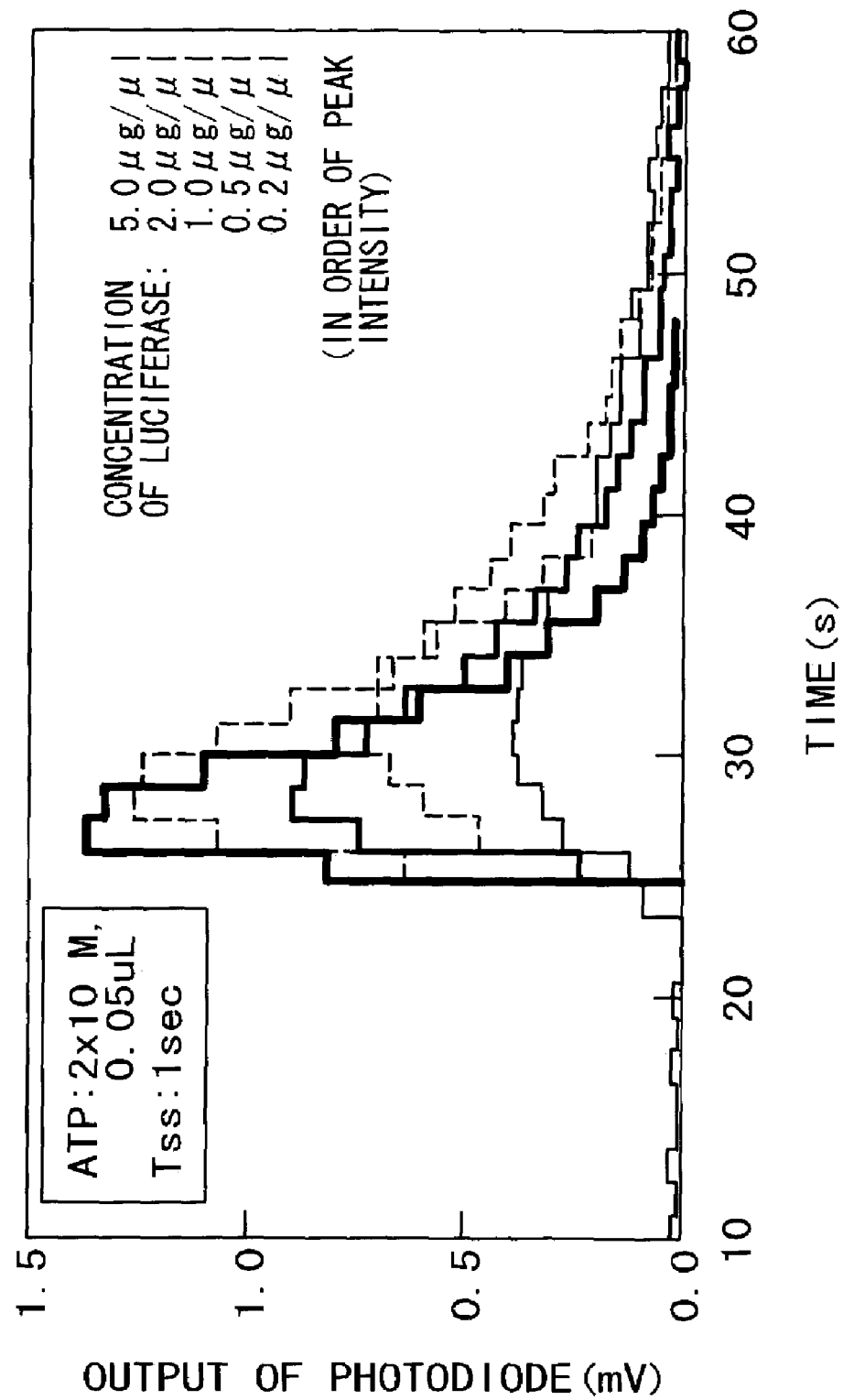
Figure 12A:
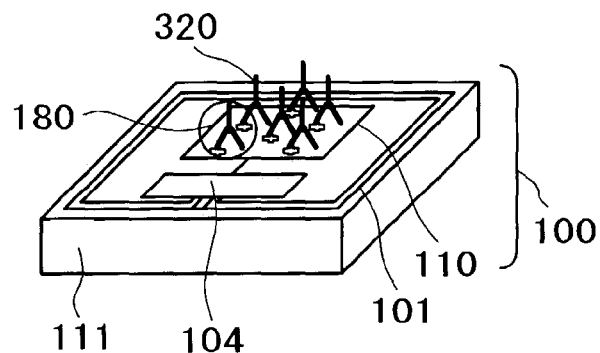
Figure 12B:
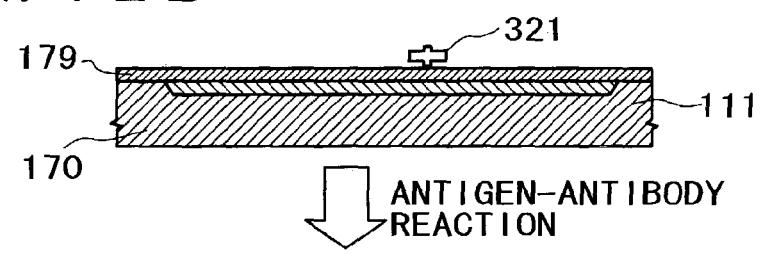
Figure 12C:
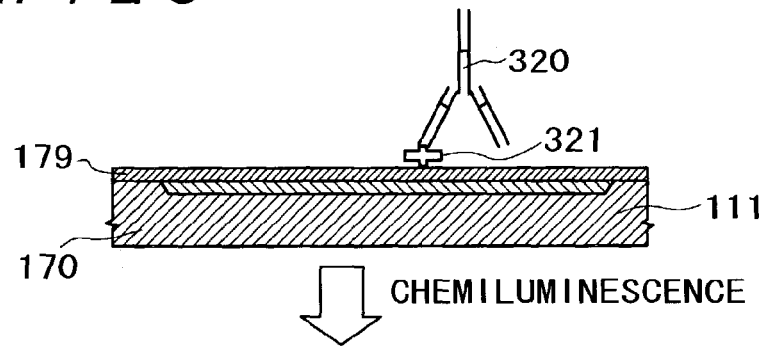
Figure 12D:
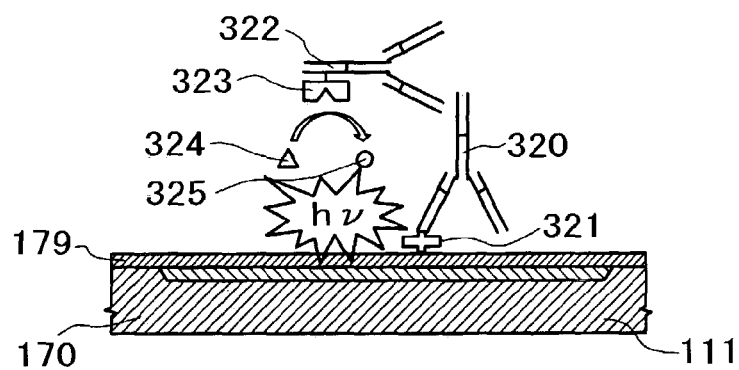
Figure 13A:
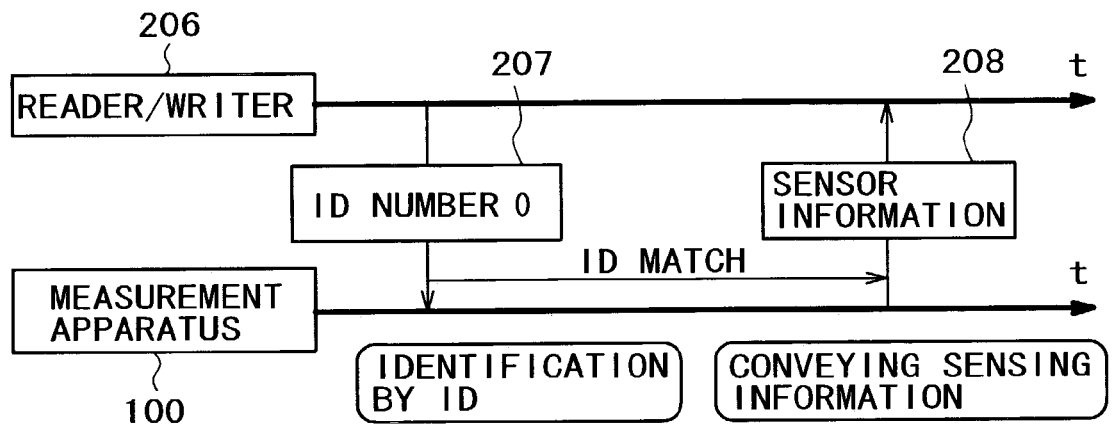
Figure 13B:
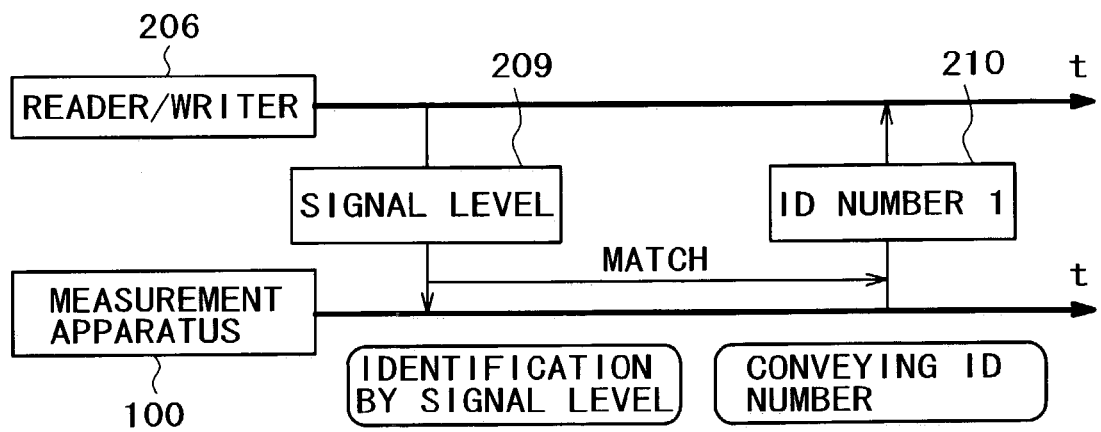
Figure 15A:
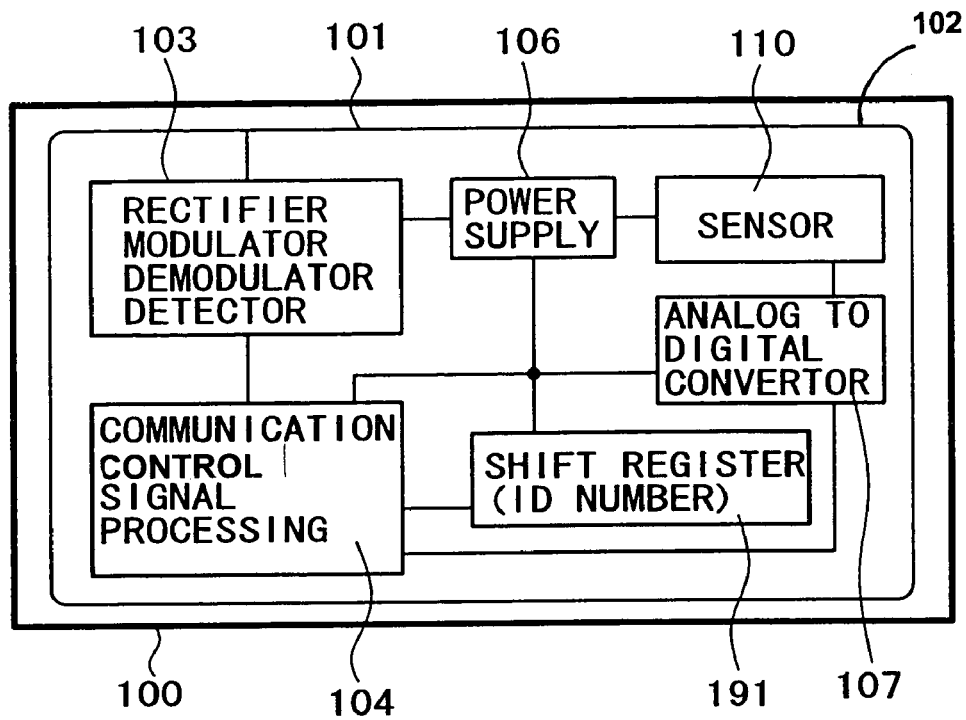
Figure 15B:
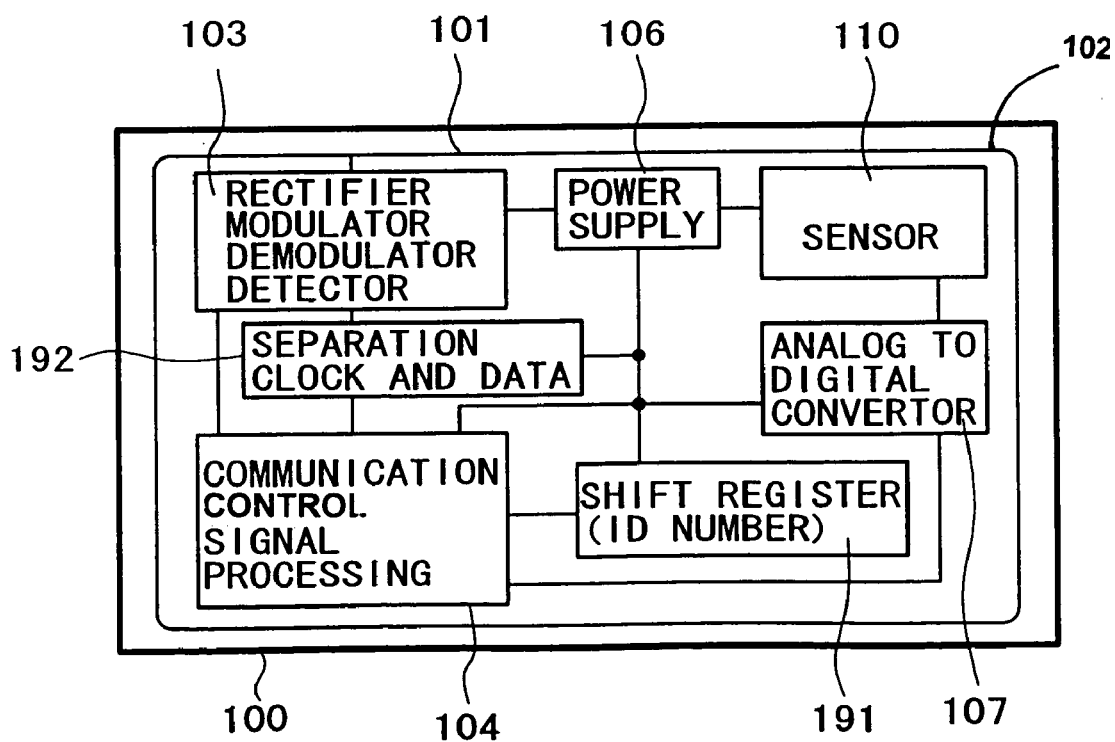
Figure 19A:
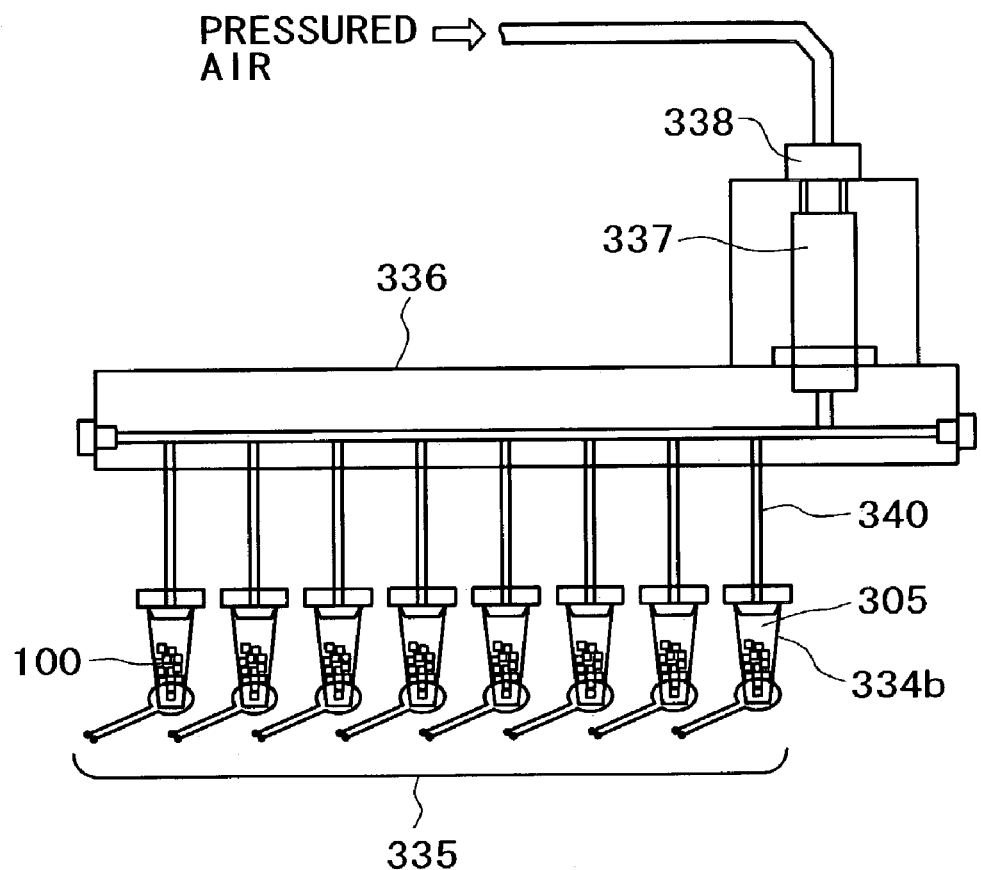
Figure 19B:
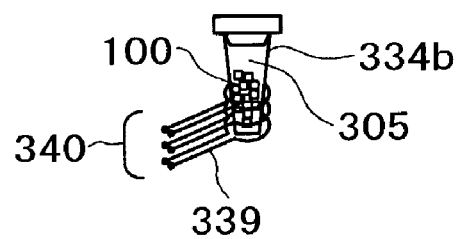
Figure 19C:
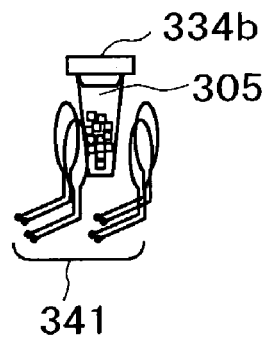
Figure 20A:
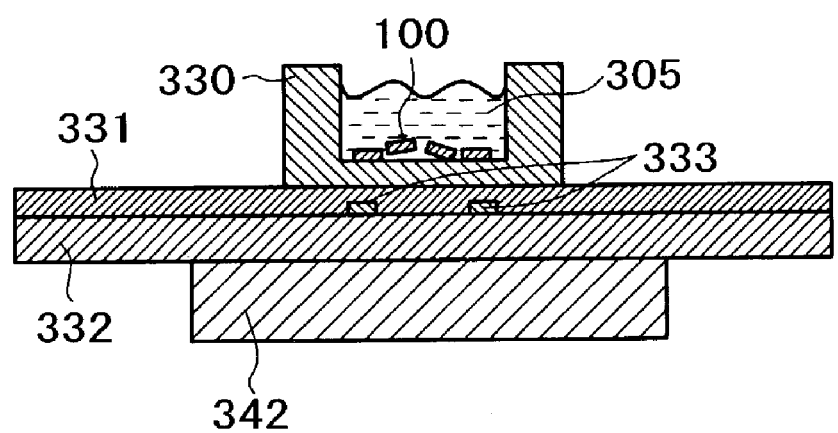
Figure 20B:
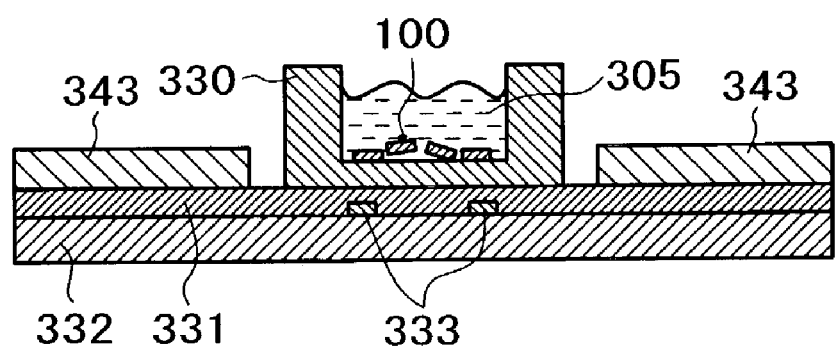
Figure 21A:
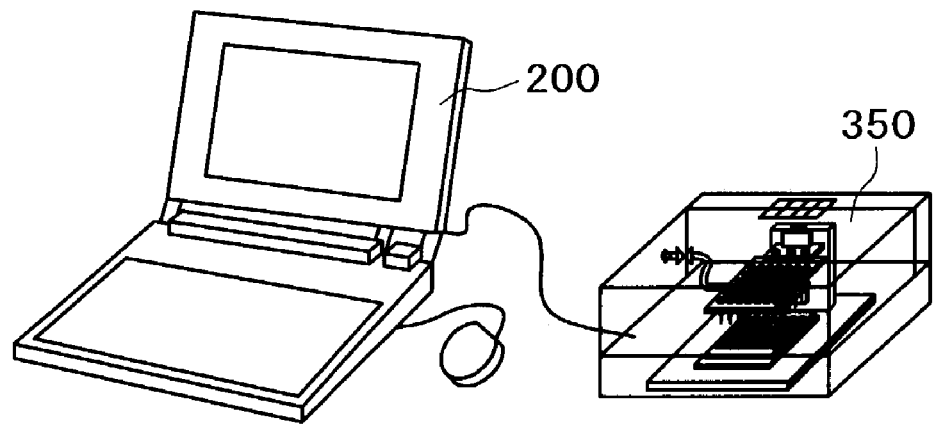
Figure 21B:
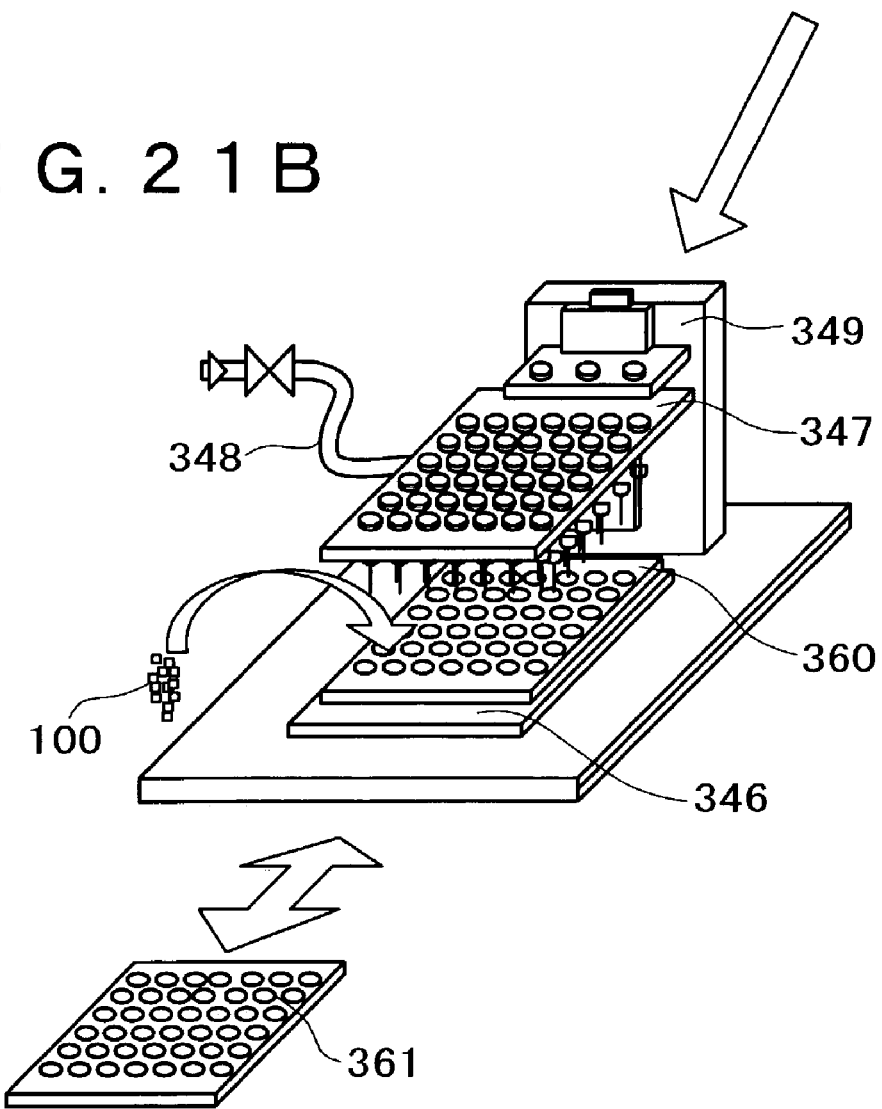

FIG; 4C is a view showing an interlayer formed between the silicon thin film and the substrate;

FIG. 5A is a view showing a sensing method using a MOSFET structure according to the embodiment 5 of the present invention;

FIG. 5B is a view showing a sensing method, in which impedance is measured between a couple of electrodes interdigitated;

FIG. 5C is a view showing a sensing method in which electrochemical reactions are applied using an intercalator according to the embodiment 7 of the present invention;

FIG. 6A is a view showing the configuration of a circuit for converting sensor signals to electric signals using a FET depending on the embodiment 8 of the present invention shown in FIG. 5;

FIG. 6B is a view showing the transistor source, on which the probe matched with the intended target is connected to one of the inputs of a couple of differential amplifier FETS;

FIG. 7A is a measurement apparatus of a procedure for typing SNPs using a photodiode as a sensor according to the embodiment 9 of the present invention;

FIG. 7B is a procedure of measurement of chemiluminescence for typing SNPs;

FIG. 7C is an emission mechanism of chemiluminescence;

FIG. 8A is a view showing the configuration of a circuit for reading out signals from a photodiode according to the embodiment 9 of the present invention;

FIG. 8B is a schematic illustration of the photodiode and readout circuit of FIG. 8A;

FIG. 9A is a view illustrating optical yields between a light source of a photodiode and a distance from the light source according to the embodiment 9 of the present invention;

FIG. 9B is a graph plotting the relationship between the distance h and the optical yield of FIG. 9A;

FIG. 10A is a side view of the structures of a reaction cell for making reaction to measure SNPs and a dispenser according to the embodiment 9 of the present invention;

FIG. 10B is a top view of the structures of a reaction cell for making reaction to measure SNPs and a dispenser according to the embodiment 9 of the present invention;

FIG. 11 is a view showing the result of chmiluminescence detection according to the embodiment 9 of the present invention;

FIG. 12A is a view illustrating enzyme immunoassay (EIA) using the measurement apparatuses of the present invention according to the embodiment 11 of the present invention;

FIG. 12B is a view illustrating enzyme immunoassay (EIA) using the measurement apparatus on which an antigen is bound on a photodiode;

FIG. 12C is a view illustrating enzyme immunoassay (EIA) using the measurement apparatus on which a primary antibody is bound to the antigen;

FIG. 12D is a view illustrating enzyme immunoassay (EIA) using the measurement apparatus with an emission of chemiluminescence by an enzyme reaction;

FIG. 13A is a view showing a flow for sending or receiving signals between an external control unit and a target measurement apparatus according to the embodiment 12 of the present invention;

FIG. 13B is a view illustrating the method according to the embodiment for sending specific level of signals from the external control unit and for sending the identification number from the measurement apparatus containing the sensor information corresponding to the signal level to the external control unit;

FIG. 14 is a view showing the configuration of a mechanism for storing sensor information converted into digital signals at an analog/digital converter and sending them via a signal processing/communication control block as needed according to the embodiment 13 of the present invention;

FIG. 15A is a view illustrating the embodiment using a shift register as a device for recording identification numbers;

FIG. 15B is a view illustrating the embodiment integrating a clock data separation circuit;

FIG. 16A is a view illustrating the embodiment comprising a circuit block for generating clock signals;

FIG. 16B is a view illustrating the embodiment using some of clocks generated for driving sensors;

FIG. 17 is a view illustrating a process flow for assembling elements to fabricate measurement apparatuses according to the embodiment 16 of the present invention;

FIG. 18 is a view showing the configurations of a sample and reagent dispenser and an external control unit for measuring many samples concurrently according to the embodiment 17 or the present invention;

FIG. 19A is a view illustrating the embodiment of a system for measuring samples in plural tubes according to the embodiment 18 of the present invention;

FIG. 19B is a view of an example of the antenna layout, in which plural antennas are closely arranged in the same direction;

FIG. 19C is a view of the layout of antennas arranged around the tubes in another direction;

FIG. 20A is a view illustrating the embodiment of a vibrator underneath the reaction cell for applying mechanical vibration to a substrate, on which external antennas are formed according to the embodiment of the present invention;

FIG. 20B is a view illustrating the embodiment of a vibrator the level of the bottom of the reaction for applying mechanical vibration to a substrate, on which external antennas are formed according to the embodiment of the present invention;

FIG. 21A is a view showing the configuration of a measurement system according to the embodiment 20 of the present invention; and FIG. 21B is a view showing the configuration of the agent disperser in a shielded box, the reaction cell containing the sample solution and the measurement apparatuses, and the integrated external antennas.

DESCRIPTION OF THE PREFERRED EMBODIMENTS

An invention for system and method for detecting biological and chemical material is disclosed. Numerous specific details are set forth in order to provide a thorough understanding of the present invention. It will be understood, however, to one skilled in the art, that the present invention may be practiced without some or all of these specific details.

In this description, the configuration of the small-sized measurement apparatus with a high sensitivity is disclosed, which has the probes for capturing biological materials such as nucleic acid and proteins fixed on the chip, on which the function block having a sensor, identification number, and radio communication mechanism are arranged, and which the presence of the target to be captured on the prove is detected by the sensor and the result of sensing is transmitted to the external control unit by the radio communication mechanism. The device for reading identification numbers and sensor signals by device of an electromagnetic wave, a change in the magnetic field, or a change in the electric field in measuring using the measurement apparatuses is disclosed.

(Embodiment 1)

Figure 1A:
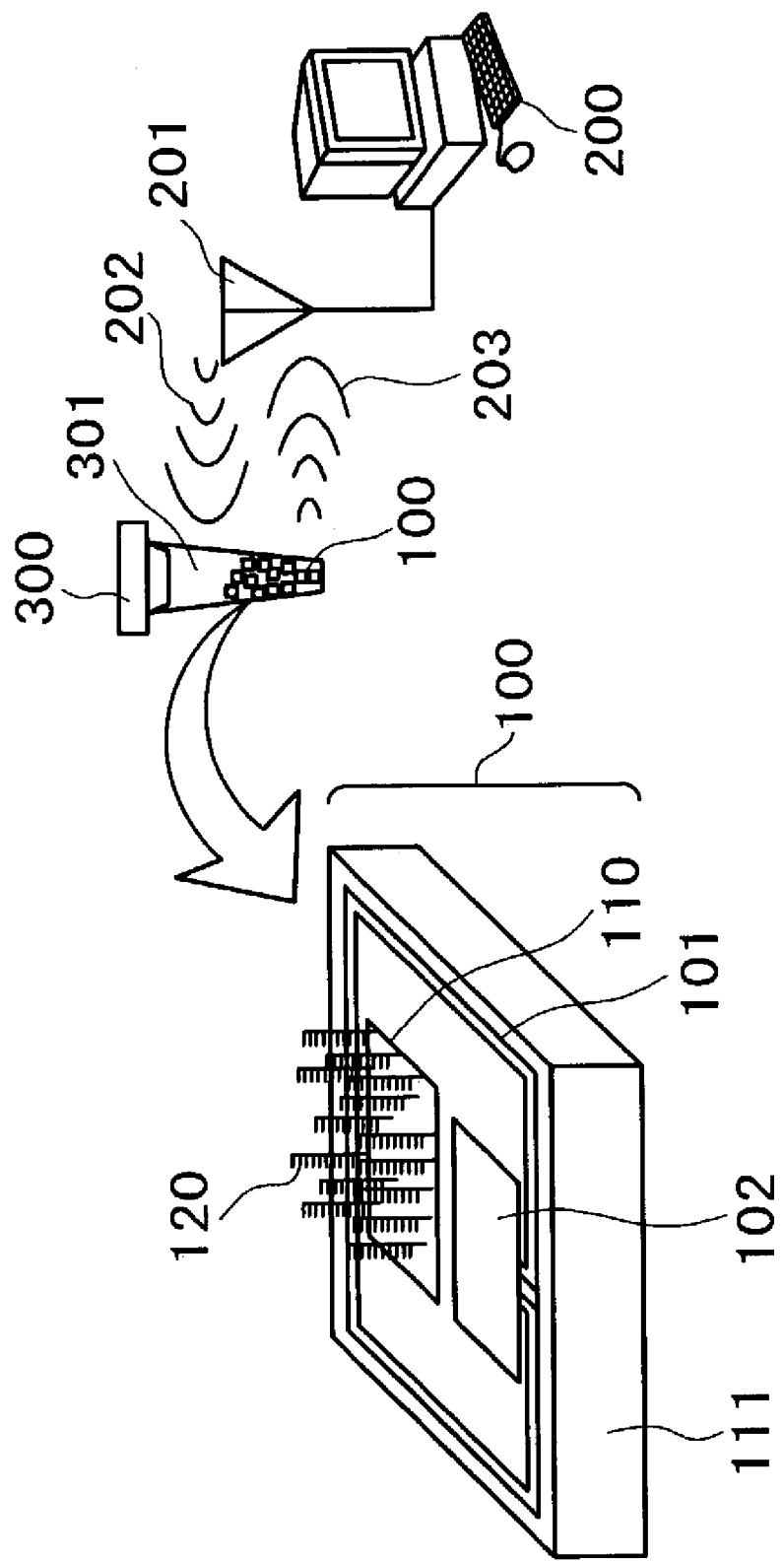
FIG. 1A is a view showing a chemical sample measurement system using a biological and chemical sample measurement apparatus according to embodiment 1 of the present invention.

FIG. 1A shows a chemical measurement system using a biological and chemical material measurement apparatus 100 of the present invention. In the measurement apparatus 100, a probe 120 appropriate for a target to be detected is fixed, a sensor 110 for detecting the target captured by the probe, a circuit block 102 having the functions for processing sensor information, controlling communication with the external control unit 200, storing and matching identification numbers, and generating and controlling power, and an antenna 101 for communicating with the external control unit are mounted on the same substrate 111. FIG. 15A is a view illustrating the embodiment using a shift register as a device for recording identification numbers and FIG. 15B is a view illustrating the embodiment integrating a clock data separation circuit.

FIG. 1B shows the function block of the measurement apparatus 100. The measurement apparatus 100 is put in a sample vessel 300 containing a sample solution 301. In the measurement apparatus 100, a sensor 110 is formed for detecting the presence or the amount of the target captured by the probe 120 fixed partially or entirely on the surface of the measurement apparatus 100. In FIG. 1, the probe is fixed only in the sensor area 110 but in fact, it may be fixed partially or entirely on the front and back surfaces and the sides of the measurement apparatus 100 in addition to the sensor area 100. On the surface of the measurement apparatus 100, a protective film is coated except for the sensor area 110 because the probes fixed on the protective film do not significantly affect the behavior of the measurement apparatus. The signals detected by the sensor are converted into digital electric signals by an AD converter (ADC) 107. In this case, it is reasonable from an aspect of designing an integrated measurement apparatus that the resolution of the ADC are set to one (two values)—eight bits (256 values). When the resolution is set to one bit, the configuration of the ADC is the same as that of a comparator, taking an advantage in power consumption, and chip occupation area. By setting to a larger number of bits, outputs can be obtained from the sensor at a high resolution but power consumption and the chip occupation area increase. On the other hand, the external control unit 200 sends the identification number (0) for identifying a specific measurement apparatus among plural measurement apparatuses 100 by device of an electromagnetic wave, a change in the magnetic field, or a change in the electric field 202. The identification number is transmitted to the plural measurement apparatuses in the sample vessel 300, received by the antenna 101 mounted on each measurement apparatus 100, and after passing through the rectifying and demodulating circuits, and matched against the measurement apparatus-specific identification number (1) 105 pre-written in the measurement apparatus 100. Matching is performed in the matching circuit in the control circuit block 102 of each measurement apparatus. When the identification number sent from the external control unit is matched against the pre-written identification number and match is established between them, the measured signals are transmitted from the measurement apparatus, in which match is achieved, through the communication control/signal processing circuit block 104 and modulation circuit block 103 via the antenna 101 to the external control unit by device of an electromagnetic wave, a change in the magnetic field, or a change in the electric field 203 for reading in. The power consumed by the control circuit block 102 and the sensor is supplied from the DC power source comprising rectifying and smoothing circuits in the control block and a voltage regulator when an electromagnetic wave sent externally, a change in the magnetic field, or a change in the electric field is received via the antenna 101.

(Embodiment 2)

Figure 2A:
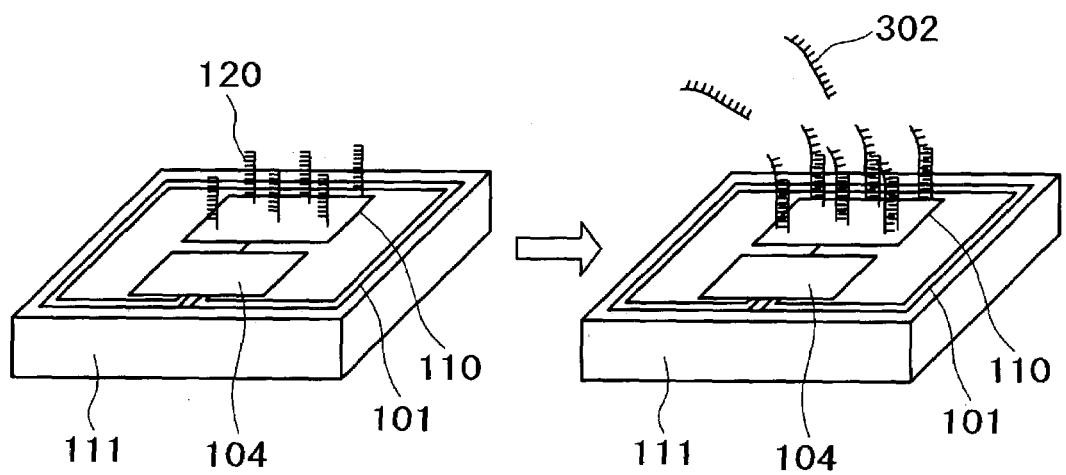
FIG. 2A is a view showing the configuration of measurement apparatuses using various nucleic acid probes according to embodiment 2 of the present invention.
Figure 2B:
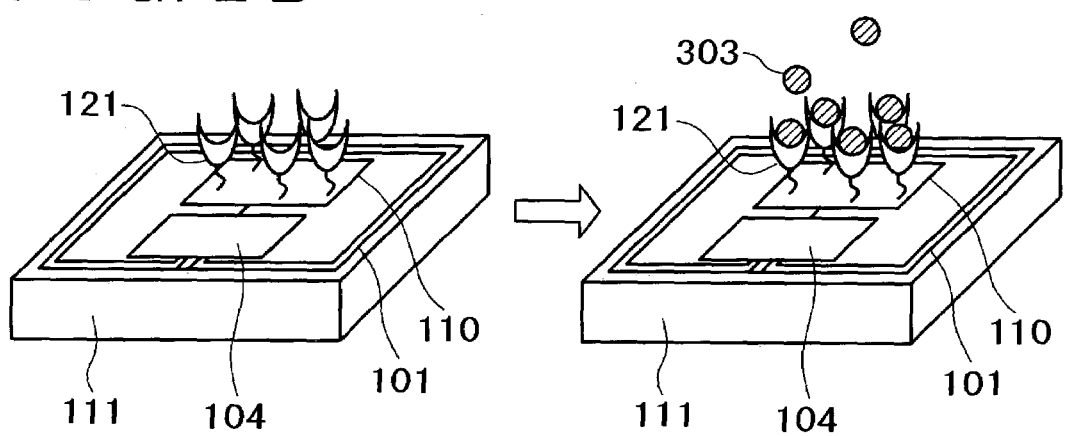
FIG. 2B is a view showing the configuration of measurement apparatuses using various protein or antibody probes according to embodiment 2 of the present invention.
Figure 2C:
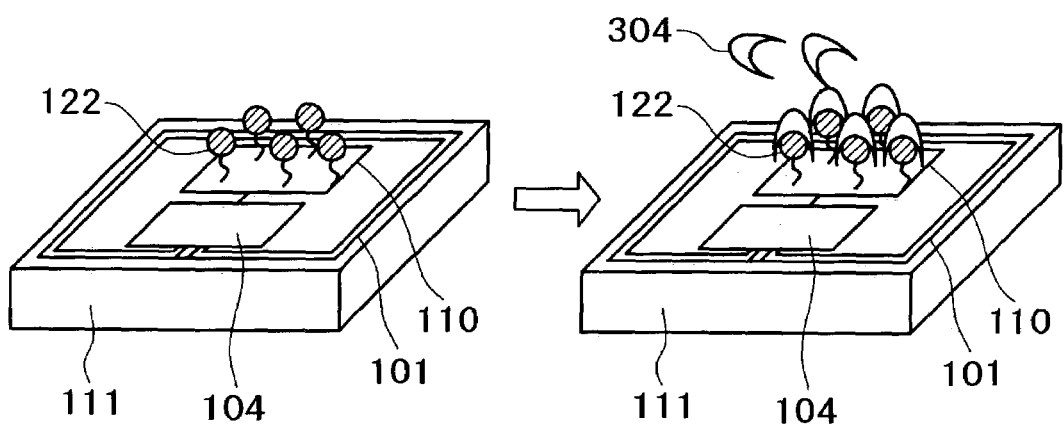
FIG. 2C is a view showing the configuration of measurement apparatuses using various antigen probes according to embodiment 2 of the present invention.

With reference to FIG. 2, the probe fixed on the measurement apparatus 100 according to an aspect of the present invention is described. In FIG. 2A, the fractions of nucleic acid are use as probes. Synthesized oligo DNAs and cDNAs may be used for nucleic acid. In FIG. 2B, an example, in which proteins or antibodies are used for probes, is given In FIG. 2C, antigens are used for probes.

(Embodiment 3)

Figure 3:
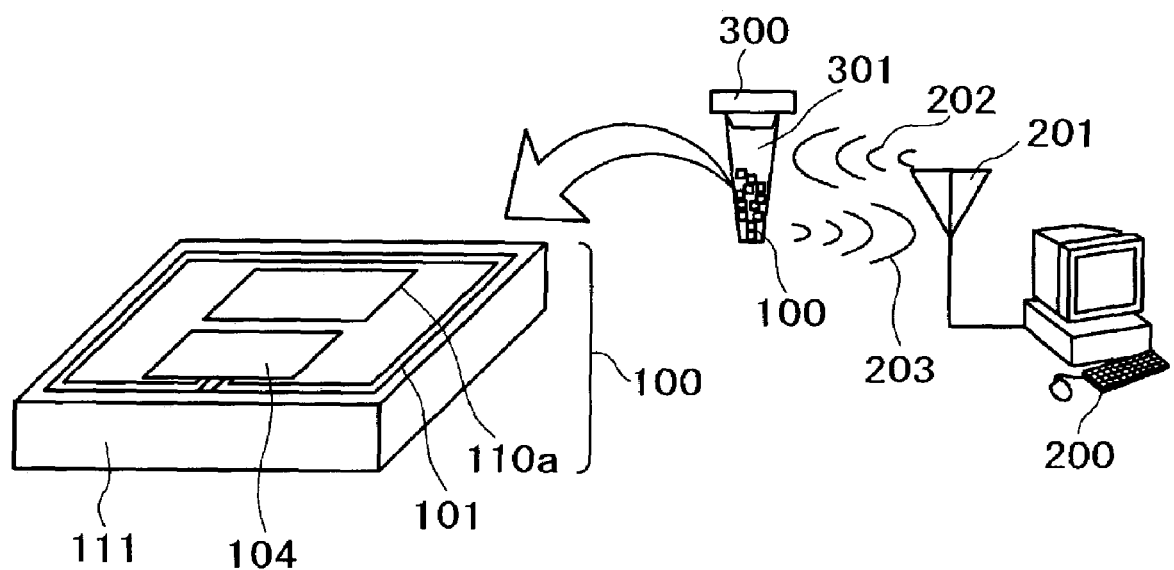
FIG. 3 is a view showing the configuration of measurement apparatuses for measuring physical and chemical amounts without using probes as sensors according to the embodiment 3 of the present invention.

For the sensor mounted on the measurement apparatus 100, the type for measuring physical and chemical amounts in the location the measurement apparatus is disposed may be used as shown in FIG. 3, instead of the type for measuring coupling by affinity of the probes with the targets in the sample solution using the probes as shown in FIG. 1. For example, the sensor for measuring temperature, pressure, amount of light, pH, ion concentration or sugar may be used.

In measuring temperatures, temperature-dependency of semiconductor resistivity or diode voltage-voltage characteristic may be used. In measuring pressures, the sensor using a microdiaphragm structure implemented by the piezoelectric element or MEMS (micro electromechanical systems) technology may be used. In measuring the amounts of light, a photosensor using a change in semiconductor conductivity by photodiode or light excited carriers may be used. In measuring pH and ion concentrations, an ion sensitive film, which captures specific ions to change electromotive force, may be used.

The physical and chemical amounts measured by the sensors mentioned above, after converted into electric signals by the method and the similar device described in the embodiment 1, are digitized, modulated, and sent from the measurement apparatus 100 based on the identification number sent from the external control unit.

(Embodiment 4)

In the embodiment, a substrate to be used for the measurement apparatus 100 is described. The measurement apparatus comprises the function blocks including a sensor, an antenna, a detection circuit, a rectifying/modulating/demodulating circuit, and a communication/data processing/storage control circuit. By integrating these function blocks on one chip, a small-sized and light-weight measurement apparatus can be implemented while the process and assembly costs are minimized. This type of functions can be implemented by mounting part of the function block on the separated chip and integrating these chips onto a printed circuit substrate.

When the function blocks mentioned above are mounted on the same substrate, a silicon substrate can be used.

As shown in FIG. 4A, the use of the silicon substrate allows the elements and structures making up the function blocks mentioned above to be mounted according to the commonly used prior art. The function blocks of the rectifying/modulating/demodulating circuit and the data processing/storage circuit can be implemented by the integrated circuitry technology using CMOS transistors.

FIG. 4B is a view showing the insulative substrate 114 such as glass, quartz, and ceramics, on which a thin silicon film are applied. For example, a thin film of polycrystalline silicon may be applied on a sapphire substrate by the CVD (chemical vapor deposition) process and extended again by the zone melt process to obtain a monocrystalline silicon of thin film.

In FIG. 4C, an interlayer is formed between the silicon thin film and the substrate. Monocrystalline silicon and ceramics may be used for the substrate. For example, by employing such a structure that monocrystalline silicon is used for the substrate and a SOI (Silicon on insulator) using a $SiO_2$ film is used for the interlayer, any parasitic capacity in a MOS transistor source, gate, and wiring can be reduced, resulting in low power consumption. As a result, a small amount of power supplied externally may be sufficient, which enables the size of an antenna to be reduced mounted on the measure apparatus 100.

In this case, it is preferable that the length of the longest side of the measurement apparatus 100 does not exceed 3 mm. By keeping the measurement apparatus smaller, it may be put on the microtiter plate or tube with a length of 100 µl.

(Embodiment 5)

An aspect of the sensor mounted on the measurement apparatus 100 according to the present invention is described.

FIG. 5A shows an example of the sensor using a field-effect transistor (FET). The FET with a MOS structure is mounted on the silicon substrate 111. This means that a source area 133 is separated from a drain area 134 by a gate area, which comprises a gate electrode 131 made of a conductive material and a gate insulating film 132. A probe 120 is fixed on the gate electrode. Assuming that a target is DNA fractions, when a target 302 is trapped on the probe 120 through hybridization, the potential of the electrode changes because DNAs are negatively charged, which in turn affects the conductivity of a FET channel area 136. According to the method disclosed as an embodiment in Journal of Physical Chemistry B vol. 101 (1997) p. 2980–2985 by Souteyrand, E., et al., the probe is fixed in at least the area containing the gate, hybridized in the sample solution and then the conductivity between the source 133 and the drain 134 is measured to determine the presence or the amount of the target coupled onto the probe 120.

The present invention relates to the system for testing biological materials such as genes and to use this system, the sample preparation process is required. The sample DNAs can be obtained by, for example, extracting genome from blood and PCR amplifying plural target areas to be tested. The sample preparation method is not limited to the embodiments disclosed in this description.

The probe is fixed by the following method. A glycidoxypropyl group is introduced on the surface of the measurement apparatus 100, which is covered with a $SiO_2$ protective film by the known silane coupling reaction. The measurement apparatus 100 is submerged in 1M NaOH solution and ultra-sound cleaned for 30 minutes. The measurement apparatus 100, after washed under the pure running water, is baked at 110° C. for 15 minutes. The measurement apparatus is immersed in the concentrate 3-glycidoxypropyltrimethoxysilane solution for 5 minutes, and then in 4% 3-glycidoxypropyltrimethoxysilane solution dissolved in 50% ethanol solution for 30 minutes while being stirred sometimes. The measurement apparatus is baked at 110° C. for 30 minutes to obtain the measurement apparatus 100, of which surface a glycidoxy group has been introduced using the silane coupling reagent. 1 µl of various probes 120 appropriate for the targets to be tested (20 pmol/µl) is dissolved in 0.5 M of sodium hydrogen carbonate buffer (pH 9.5) to obtain a 1 pmol/µl solution. The measurement apparatus 100 with a glycidoxygroup introduced is immerged in the resultant solution. The measurement apparatus 100 is heated at 50° C. for 30 minute under the presence of saturated water vapor to avoid drying. The measurement apparatus 100 is taken out from the DNA solution and immersed in 0.5M of sodium hydrogen carbonate buffer (pH 9.5) containing 0.1 M Lys to block the remaining glycidoxygroup. The measurement apparatus 100 is cleaned with 20 mM of Tris-HCL (pH 7.5). Through the process mentioned above, the probe 120 containing several hundreds of probes are fixed through the reaction between 5' end amino group and the glycidoxygroup. For probes, for example, the following synthesized oligo DNAs may be used.

[p53exon8-wild type]
5'-CAG GACAG GCACA AACAC GCACC TCAAA G-3' (sequence number 1)

The following oligo DNA is used as the target for the above probe.

5'-AACAGCTTTGAGGTGCGTGTTTGTGCCT-GTCCTGGGGAGAGACCGGCGCACA-3' (sequence number 2)

In this case, probes are fixed together for each probe type on the associated plural measurement apparatus.

(Embodiment 6)

FIG. 5B shows the device for determining the presence or the amount of the captured target by measuring the impedance between a couple of electrodes disposed so that they are interdigitated. The measurement method is disclosed in Sensors and Actuators B49 (1998) p. 73–80 by Van Gerwen, P., et al. The probe 120 is fixed on the measurement apparatus 100 by the same method as that of the embodiment 5. It is immersed in the sample solution containing the targets to hybridize with the targets on the probes. The fixation of the probes and hybridization reaction are induced by the same method as that mentioned above. When the targets are coupled to the probes, modified surfaces of the electrodes change, which in turn affects the impedance between the electrodes. The presence of the target is determined by measuring the impedance.

(Embodiment 7)

FIG. 5C shows the detection process using the electrochemical reaction according to the embodiment of the present invention. As the detection method using the electrochemical reaction, for example, the method disclosed in Analytical Chemistry, vol. 66, No. 21 (1994) p.3830–3833 by Hashimoto, K., Ito, K., and Ishimori, Y. can be used. A single-strand DNA is used as the probe 120 fixed on the electrode 143. The probes can be fixed by the same method as that of the embodiment 5. Not only DNA fractions, targets, but also an intercalator 309, which is selectively trapped in a double-strand area, are added in the sample solution. When the probe 120 and the target 302 are hybridized into a double-strand DNA, the intercalator 309 is trapped in the resultant double-strand DNA, playing a central role in the oxidization/reduction reaction. In the electrodes, on which the probes are fixed, a change in current is observed due to an AC electric field caused by the oxidization/reduction reaction of the intercalator.

(Embodiment 8)

FIGS. 6A and 6B show the configuration of the circuit for converting the sensor information sent from the sensor using a FET shown in FIG. 5A into the electric signals according to the embodiment of the present invention. In FIG. 6A, the drain electrode is connected to a power source Vdd 152 and the source electrode is connected to the current source 153 in n-channel FET sensor. When the target is trapped in the probe 120, the potential of the gate electrode 131 changes relative to the substrate 111. This affects the conductivity of a channel 136 of the surface of the semiconductor substrate 111 beneath the gate electrode through the gate insulating film, resulting in a change in the potential of a terminal 164. The information on the change is transferred from a terminal 155 to the succeeding signal processing circuit through a source follower circuit consisting of a MOSFET 151 and the current source 154. In FIG. 6B, an example is given, in which the FET having the probe 120a matched with the intended target fixed and the FET having the probes matched and not matched with the intended target are mounted on the same substrate and signals are input to MOSFETs 158 and 159, a couple of differential amplifiers. In the detection process through hybridization, the signals are significantly affected by non-specific coupling, which must be eliminated. In FIG. 6B, the source 165 for the sensor FET, on which the probe 120a matched with the intended target is connected to one of the inputs of a couple of differential amplifier FETs while the source 166 for the sensor FET, on which the probe 120b not matched with the intended target is connected to another one of the inputs of a couple of differential amplifier FETs to direct the differential output between two differential amplifiers to the terminal 163. This configuration eliminates any influence by foreign substances in the sample solution, yielding signals at a high S/N ratio by selectively coupling the probe to the intended target.

(Embodiment 9)

The use of the photodiode for the sensor in the measurement apparatus of the present invention allows SNPs to be measured by the BAMPER method. The embodiment of the present invention is described below. The BAMPER method has such a characteristic that it is designed so that the 3' end of the primer is positioned at the site, in which a displacement can be detected to synthesize a complementary strand. The extension of the complementary strand of the primer is largely dependent on whether or not the 3' end is matched to the target. When matched, the complementary strand extends while when not matched, the complementary strand does not almost extend. If this phenomenon is used, SNPs can be identified. However, complementary-strand synthesis may proceed even if the end base is not matched with the intended target. To prevent this, a mismatch base is automatically inserted into the vicinity of the 3' end of the primer. In this case, since two mismatches in total exist including one in the end of the primer, almost no extension of the complementary strand of this primer occurs. On the other hand, when the 3' end is matched with the intended target, complementary strand synthesis occurs with inorganic pyrophosphate released even if an artificial mismatch exists in the vicinity of the end. By inserting an artificial mismatch in the vicinity of the 3' end, complementary strand synthesis can be controlled using the match and mismatch in the 3' end at a high accuracy. The reaction formula 1 is shown below.

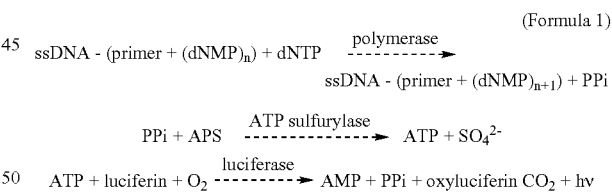

(Formula 1)

$$\text{ssDNA - (primer + (dNMP)}_n\text{) + dNTP} \xrightarrow{\text{polymerase}} \text{ssDNA - (primer + (dNMP)}_{n+1}\text{) + PPi}$$

$$\text{PPi + APS} \xrightarrow{\text{ATP sulfurylase}} \text{ATP + SO}_4^{2-}$$

$$\text{ATP + luciferin + O}_2 \xrightarrow{\text{luciferase}} \text{AMP + PPi + oxyluciferin CO}_2 + h\nu$$

Under the presence of DNA polymerase, when the DNA complementary strand of a reactive matrix dNTP (deoxyribonucleotide triphosphate) is synthesized, inorganic pyrophosphate (PPi) is produced as a by-product. When is reacted under the presence of APS (adenosine5) and ATP sulfurylase, ATP is produced. ATP reacts under the presence of luciferin and luciferase, emitting light. By measuring the light, whether the complementary strand has been extended can be determined. Since in the luminescent reaction, PPi is produced, luminescence is kept by consuming APS.

Series of FIG. 7 show the measurement apparatus 100, to which the BAMER method is applied, according to the embodiment of the prevent invention. FIG. 7A, FIG. 7B and FIG. 7C show a measurement apparatus, a procedure of measurement of chemiluminescence for typing SNPs, and emission mechanism of chemiluminescence, respectively. In this case, luminescence with complementary strand extension can be detected by the photodiode and typing of SNPs in the target site can be performed. The procedure for measuring the amount of luminescence by the photodiode is described below in brief. Series of FIG. 8 show the configuration of the circuit for reading out the signals output from the photodiode 170. FIG. 8A and FIG. 8B are readout circuit of the photodiode signal and schematic illustration of photodiode and readout circuit, respectively. Prior to measurement, signals are input to a rest signal input terminal 172 to turn on the MOSFET 171 and reverse bias is applied to the photodiode to charge up to the initial voltage Vpd. After charged, the MOSFET 171 is turned off into the signal detection mode. When light is irradiated onto the photodiode, the voltage across the photodiode terminals drops due to discharge. By monitoring this voltage, the amount of light can be determined. The voltage value of the photodiode is transferred to the signal processing circuit through the source follower circuit. If the plural measurement apparatuses of the present invention, on which different probes are fixed, are put in the same reaction cell, light derived from the extension reaction of the probe fixed on the specific measurement apparatus may cause crosstalk in the measured value for the sensor of the other measurement apparatus.

FIG. 9 is a view illustrating the relationship between the optical yield and the distance from the light source. FIG. 9A shows a solid angle subtended by a rectangular photodetective part ($2a \times 2b$) at a distance h from the light source S181. The solid angle can be expressed as shown in the following formula 2. (LICHT UND BELEUCHTU NG: Theorie und Praxis der Lichttchnik $4^{th}$ Edition by Hans-Jurden Hents hel, 1994 Huthig Buch Veriag, Heidelberg)

$$\Omega ab = 4 \sin^{-1}((ab/h^2)/(\sqrt{(1(a/h)^2}\sqrt{(1+(b/h)^2)}))\Omega 0 \quad \text{(Formula 2)}$$

$\Omega 0$: Unit solid angle (=1sr)

FIG. 9B is a graph plotting the relationship between the distance h and the optical yield obtained by calculating a solid angle $\Omega 0$ subtended by the square photodetective part with an area of 2 mm×2 mm directly under the light source and a solid angle $\Omega 1$ subtended by the adjacent square photodetective part with an area of 2 mm×2 mm at an interval of 3 mm using the formula 2. In this case, the light source S is placed directly on the intersection between the diagonals in the detector. Since this graph has a symmetry property, the angle $\Omega_0/4$ in only one quadrant in the x-y plane is calculated and multiplied by 4. When the distance exceeds 1.5 mm, the light derived from the probe fixed directly on the photodiode is reduced to 20% or less and when it exceeds 3 mm, the light is reduced to 10% or less. In fact, since an inclination of the measurement apparatus 100 is added, the solid angle becomes smaller than these values, which results in the crosstalk sufficiently reduced to determine the presence of the target captured. In this case, the PPi diffusion to the vicinity of other measurement apparatus due to the extension of the DNA captured by the specific measurement apparatus has no effect on target detection because luminance attenuates due to decrease in concentration as the distance from the light source becomes larger and because the effect of PPi diffusion can be minimized by aborting the measurement of luminance in advance.

To fix the probe on the measurement apparatus, a glycidoxypropylgroup is introduced on the $SiO_2$-coated surface of the measurement apparatus for treatment using the silane coupling reaction according to the procedure described in the embodiment 5. In this embodiment, the above probe (the primer for genome typing) is fixed. The method for fixing the probe is the same as that described in the embodiment 5. To perform typing on SNPs, the measurement apparatus, on which both of the wild type, in which single nucleotide at the 3' end has been replaced as mentioned later, and mutant type of probes have been fixed, is used. In this example, the probe for detecting SNPs present in p53exon8 is used. Alternately, the measurement apparatus 100, on which the primer with a base sequence for detecting SNP in other site has been fixed as a probe, may be selected at the same time for immersing in the reaction cell.

Now, a reagent to be used in the method and its composition are described below.

(i) Reaction solution
0.1 M Tri-acetate buffer, pH 7.7
0.5 mM EDTA
5 mM magnesium acetate
0.1% bovine serum albumin
1 mM dithiothreitol
0.2 mg/mL polyvinylpyrrolidone
0.2 U/μL DNA polymerase 1, Exo-Klennow Fragment
1.0 U/mL ATP sulfrylase
2 mG/mL luciferase
(ii) Matrix solution A
10 mM Tri-acetate buffer, pH 7.75
25 μM dNTPs
1.0 μM APS
(iii) Matrix solution B
10 mM Tri-acetate buffer, pH 7.75
20 mM D-luciferin The procedure for measuring BAMPER using synthesized oligo DNAs (with the same sequence as that of p53) as the DNA sample is described. The mutation sites are underscored in the p53 sequence. The DNA sample and the primer for genome typing described in the embodiment are shown below (both of them supplied from Amersham Pharmacia Biotech). Note that an artificial mismatch primer has been used as the primer for genome typing.

```
[p 53exon8-wild type]
5'-CTTTC TTGCG GAGAT TCTCT TCCTC TGTGC GCCGG TCTCT CCCAG GACAG      (sequence number 3)

GCACA AACAC GCACC TCAAA GCTGT TCCGT CCCAG TAGAT TACCA-3'

[p 53exon8-mutant type]
5'-CTTTC TTGCG GAGAT TCTCT TCCTC TGTGC GCCGG TCTCT CCCAG GACAG      (sequence number 4)

GCACA AACAC GCACC TCAAA GCTGT TCCGT CCCAG TAGAT TACCA-3'

[Primer for genome typing (for wild type)]
5'-AACAGCTTTGAGGTGCGTGATT-3'                                         (sequence number 5)
```

-continued

[Primer for genome typing (for mutant type)]
5'-AACAGCTTTGAGGTGCGTGATA-3'

(sequence number 6)

By hybridizing the target DNA fraction (10–100 fmol/μl) and the probe for genome typing (Primer) 120 fixed on the measurement apparatus in an annealing buffer (10 mM Tris-acetate buffer, pH 7.75, 2 mM magnesium acetate) (at 94° C. for 20 sec., 65° C. for 120 s, room temperature) the DNA sample solution is obtained. The reaction, which develops when SNPs are detected using the BAMPER method, is illustrated in FIG. 7B.

The measurement apparatuses are put in the sample solution containing target DNA fractions (10–100 fmol/μl) to hybridize with the probes fixed in the annealing buffer (10 mM Tris-acetate buffer, pH 7.75, 2 mM magnesium acetate) on the measurement apparatuses (at 94° C. for 20 sec., 65° C. for 120 sec, room temperature). The measurement apparatuses, on which the probes hybridized with the sample DNA fractions are fixed, are put in the reaction solution mentioned above (40 μl) and the matrix solution A (10 μl) is added to it to induce the base extension reaction. In this case, different probes such as 120c and 120d are fixed on the plural measurement apparatuses put in the reaction cell 330. 2 second after the initiation of base extension, the matrix solution B (1 μl) 306 is added using a dispenser to induce the chemiluminescence.

FIG. 10A shows the configuration of the reaction cell 330 and the dispenser 307 used in the reaction mentioned above. A capillary tube 308 with an internal diameter of 25 μm and a length of 21 mm is used as the dispenser. By changing the pressure value and pressure time, the amount of the matrix solution to be added can be controlled at a high accuracy. When the amount of the matrix solution is 0.1 μl, the pressure is set to 0.2 MPa and the pressure time is set to 1.1 sec. The base extension reaction was controlled using match and mismatch at the end of the primer, luminescence was observed in the reaction cell 330. This suggested that the sequence corresponding to the primer in the reaction cell sit on the target DNA. Luminescence was detected by the photodiode on the measurement apparatus 100, converted into an electric signal, and transferred by device of any of an electromagnetic wave, a change in the magnetic field, or a change in the electric field. The signal sent out from the measurement apparatus 100 is received at the external antenna 333 and passed to the external control unit. As shown in FIG. 10A and FIG. 10B, by placing the external antenna close to the measurement apparatus 100 outside of the reaction cell 330 as possible, attenuation in signal due to an electromagnetic wave, a change in the magnetic field, or a change in the electric field can be prevented.

(Embodiment 10)

In the embodiment 9, the method for measuring SNPs using chemilluminescence was disclosed. In this example, the method is described with reference to the measured data on the dependency on lucipherase concentration. According to the formula shown in the embodiment 9, luminescence is induced by the reaction, during which luciferin is oxidized under the presence of ATP and lucipherase.

(Formula 3)

ATP + luciferin + $O_2$ $\xrightarrow{\text{luciferase}}$ AMP + PPi + oxyluciferin + $CO_2$ + hv The setup of the measurement apparatus shown in FIG. 10 was generally used with an exception that the measurement apparatus was placed outside of and directly beneath the reaction cell closely and signals are read out via a lead line.

Specifically, the AP solution (2×10−7 M, 0.05 μl) is added to the matrix solution, which is the buffer (10 mM Tris-acetate buffer, pH 7.75) with lucipherin (0.1 μg/μl) and lucipherase (0.2, 0.5, 1.0, 2.0, and 5.0 μg/μl) dissolved. By observing changes in signal with time assuming that a signal accumulation time Tss was one sec., the dependency on lucipherase concentration could be obtained. FIG. 11 shows the result of the measurement. As the concentration of lucipherase becomes higher, the time constant for the reaction decreases, and the peak intensity increases. The maximum variation of the output from the photodiode is 1.4 mV and by amplifying this, analog/digital conversion can be easily made.

It was verified that the function for radio communication read the identification numbers correctly at a frequency of 13.56 MHz using the buffer mentioned above (10 mM Tris-acetate buffer). Since the measurement apparatus is coated with any protective film such as $SiO_2$ and $Si_3N_4$ films, the communication function block inside the measurement apparatus works normally even in the solution. The communication distance achieved by the measurement apparatus in the buffer was 70–80% of that in the air.

(Embodiment 11)

Series of FIG. 12 show the procedure for performing enzyme immunoassay (EIA) according to the embodiment of the present invention. FIG. 12A, FIG. 12B, FIG. 12C, and FIG. 12D show measurement apparatus, antigen bound on a photodiode, primary antibody bound to the antigen, and emission of chemiluminescence by an enzyme reaction, respectively. Consulting with Short Protocols in Molecular Biology 3$^{rd}$ edition edited by F. M. Ausubel, R. Brent, R. B. Kingston, D. D. Moore, J. G. Seidman, J. A. Smith, and K. Struhl, John Wiley & Sons 1995, which is a basic protocol, chemi- and bio-luminescence is used for measuring the oxygen activity. In the EIA technique, the absorption or luminescence is commonly used. Luminescence improves sensitivity, enabling antibodies and antigens to be quantified at a high accuracy (Arakawa, H., Maeda, M., and Tsuji, A.,: Anal. Biochem., 97, p 248 1979 or Puget, K., Michelson, A. M and Thore, A; Anal. Biochem., 79, p 447, 1977). In this embodiment, the method for measuring luminescence (hv=425 nm) by peroxidase using the matrix solution of luminor and $H_2O_2$ is described. The measurement apparatus 100 is immersed in the antigen solution diluted to 0.2–10 μg/ml with PBS containing 0.05% (w/v) $NaN_3$, incubated at 37° C. for 2 hours, coated with the antigen 321. The measurement apparatus, after washed with water two times, is immersed in the physiological saline with 1 mM EDTA 0.25% (w/v) BSA (bovine serum albumin) and 0.05% (w/v) $NaN_3$ added at room temperature at room temperature for 30 minutes and then washed with water three times. A primary antigen 320 (target to be analyzed) obtained from the target sample is diluted to 50 μl with blocking buffer mentioned above. The measurement apparatus 100 is immersed in this solution at room temperature for 2 hours for incubation, causing the primary antigen and the antibody to react one another. The measurement apparatus 100 is washed three times with water, immersed in the blocking buffer at room temperature for 10 minutes, and washed three times with water, and then swished water off. Next the measurement apparatus 100 is immerged in the diluted solution containing, for example, goat-antigens-rabbit igG Olsson T., Brunius, G., Carlsson, H. E., and Thore, A. J. Immunol. Methods, 25, p 127 1979) marked with peroxidase as a conjugate the secondary antigen 322-enzym 323 at room temperature for 2 hours or more for incubation, and then washed three times with water.

To prepare the matrix solution 324, luminor is dissolved in 0.1 N NaOH to obtain a 0.05 M solution and diluted with 0.2 M Tris buffer to 0.01 M. The configuration shown in FIG. 10 may be used for the reaction cell and the dispenser. The same amounts of 0.2 M Tris buffer (pH 8.5) and 0.01 M $H_2O_2$ solution are poured into the reaction cell. The measurement apparatus 100 mentioned above is put into the solution and the luminor diluted solution above is dropped in it. Luminescence is detected by the photodiode shown in the FIG. 8. In this case, by immersing the measurement apparatus 100 in the solution containing the primary antigens obtained from the different sample (the primary antigen sample is different) and measuring, many samples can be evaluated under the same condition simultaneously.

(Embodiment 12)

The use of the measurement apparatus 100 of the present invention enables many items such as SNPs and different kinds of proteins at the several sites on the genome to be tested to be measured simultaneously by putting plural measurement apparatuses 100 in the one reaction cell as mentioned in the embodiment 8. In this case, the signals detected at the plural measurement apparatuses must be individually identified and read into the external control unit 200. In the embodiment 1, the method for sending the identification number 207 of the measurement apparatus 100 by the external control unit 200 by reader/writer 206, receiving it by the measurement apparatus 100, and sending the sensor information based on the result of matching with the identification number stored in the measurement apparatus 100 is described. The flow of signal sending/receiving is described in the embodiment.

FIG. 13A shows the flow of signal sending/receiving when the identification number of the target measurement apparatus 100 is sent from the external control unit 200 by reader/writer 206. The identification number of the target measurement apparatus 100 is sent from the external control unit 200 by reader/writer 206 to the plural measurement apparatuses 100. Individual measurement apparatuses determine matching of a received signal against the identification numbers stored in the apparatuses. If not matched, the measurement apparatus 100 stops. If matched, the sensor information is sent. When the signals are sent from the external control unit 200 by reader/writer 206 to the measurement apparatus 100 serially, the identification number sent is matched with the stored identification number bit by bit. If not matched at any point, the measurement apparatus 100 stops the matching process. On the other hand, as long as the bits sent are matched with the bits of the identification numbers written in individual measurement apparatuses serially, individual measurement apparatuses continue matching. If all of the bits sent are matched with those stored in the apparatuses, the measurement apparatus sends sequentially the sensor information.

FIG. 13B is a view illustrating the method according to the embodiment for sending specific level of signals from the external control unit 200 by reader/writer 206 and sending the identification number from the measurement apparatus 100 containing the sensor information corresponding to the signal level to the external control unit 200 by reader/writer 206.

(Embodiment 13)

FIG. 14 shows the configuration of the function block according to the embodiment, in which the sensor information converged-into digital signals at the analog-digital converter (ADC) 107 are stored in memory 190 and sent from the measurement apparatus through the signal processing/communication control block. In this case, the sensor information may be only one value at a point or may be plural values at several time points. The apparatus-specific identification number could be stored at the given addresses in memory.

By mounting memory for storing the sensor information temporarily, plural data obtained at several time points can be stored and sent together. In this case, the maximum, minimum, and average within a given time period can be recorded and sent even if the measurement apparatus does not always or frequently communicate with the external control unit 206.

(Embodiment 14)

FIG. 15A is a view of the configuration of the function block of the measurement apparatus 100 according to the embodiment of the present invention. In this example, a shift register is used as a device for recording the identification numbers. When the number of bits for identification number is about 10, the circuit can be more easily configured for recording and matching the identification numbers than memory.

FIG. 15B is a view of the configuration with a clock data separation circuit according to the embodiment of the present invention. In this case, a clock for driving the circuit must be inserted in the circuit block 102 on the measurement apparatus 100. Preferably, the power consumed by the circuit block 102 on the measurement apparatus 100 is supplied externally by device of an electromagnetic wave, a change in the magnetic field, or a change in the electric field and the circuit is simplified for power saving. To do so, a clock can be generated at the external control unit 200 (illustrated in FIGS. 1A and 1B) to send to the measurement apparatus by device of the carrier. At the circuit function block 192, sent clock signals and data signals are separated and the resultant clock signals are used for driving the individual circuit blocks.

(Embodiment 15)

FIG. 16A is a view illustrating clock signal generation on the measurement apparatus 100. Clock signals are generated from an electromagnetic wave, a change in the magnetic field, or a change in the electric field received at the antenna on the measurement apparatus 100. For this reason, optimal clocks can be generated for each measurement apparatus. The clocks appropriate for the circuit blocks on the measurement apparatus can be generated.

FIG. 16B is a view illustrating clock signal generation. In this case, some of clock signals generated on the measurement apparatus 100 are used for driving the sensor. To measure the impedance between the microelectrodes described in the embodiment 6, an AC or pulse power source must be mounted. In this case, a circuit 193 for generating clocks from an electromagnetic wave, a change in the magnetic field, or a change in the electric field received at the antenna 101 is inserted. The clocks generated at the circuit 193 is used to measure the impedance between the microelectrodes. Since the electromagnetic wave received is generally 1 MHz or higher, the clocks can be obtained by dividing it. Alternately, the clocks can be generated by an oscillator from the DC power source described in the embodiment 1.

(Embodiment 16)

FIG. 17 shows a flow of assembling elements for building the measurement apparatus 100. Using CMOS for the circuit mounted on the measurement apparatus enables high density package and power consumption. For this reason, the CMOS assembling process is critical. FIG. 17 shows an example of the process for assembling the measurement apparatus using the photodiode for the sensor described in the embodiment 8 according to the embodiment of present invention. An element separation area is formed on a silicon substrate, the photodiode and MOSFET are mounted, lines are wired, and finally the protective film is applied.

When the FET-structured sensor described in the embodiment 6 is used, the commonly-used CMOS gate electrode part of the circuit should be so assembled using a material suitable for probe fixation that it can be in direct contact with the solution containing targets with no protective film.

The antenna 101 is formed in the metallization process on the second and third layers (process number 8). If metallization on 2–3 layers or more is required to build the MOSFET circuit, the antenna is formed across these layers in another process. No magnetic field lines pass through conductive layers such as element assembling and metallization parts on the measurement apparatus 100. For this reason, to form the antenna, the thickness of an interlayer insulating film is controlled so that the magnetic field lines can escape from the measurement apparatus 100 through the film.

(Embodiment 17)

FIG. 18 is a view showing the configurations of a sample/agent dispenser for measuring many samples concurrently and an external antenna. In this specification, the embodiments having characteristics useful in implementing a small measurement apparatus are described. These embodiments may be easily applied to large-scaled systems capable of processing many samples. By loading the measurement apparatuses of the present invention in the reaction cells on the standard microtiter plate 334a together many samples and dropping agents in them, the hybridization, affinity coupling, and luminescent reaction are induced. These reactions are detected by the sensors on the measurement apparatuses and the sensor information is read by the external antenna formed for each reaction cell.

(Embodiment 18)

FIG. 19A is a view of a measurement system for measuring samples in plural tubes 334b according to the embodiment of the present invention. The method for measuring samples is the same as that of the embodiment 14. The layout of the external antenna is described below. FIG. 19B is a view of an example of the antenna layout, in which plural antennas are closely arranged in the same direction. This layout enables the antennas to communicate with the measurement apparatuses 100 disposed at vertically various positions in the tubes at a higher efficiency. FIG. 19C is a view of the layout of antennas arranged around the tubes in another direction. This layout enables the antennas to communicate with the measurement apparatuses 100 disposed in the solution 305 in the tubes 334b in the various directions at a higher efficiency. For example, if the external antennas are arranged in three directions, which are intersected with each other, the measurement apparatuses 100 can communicate with the external antennas at a higher efficiency as well even if the measurement apparatuses 100 are oriented in the different directions.

(Embodiment 19)

Generally, if the measurement apparatuses 100 are 10 oriented in different directions, loss occurs in coupling to the external antennas, the communication distance allowed is decreased. To avoid this problem, the embodiment 19 is intended to ensure the stability of communication. As shown in FIG. 20A and FIG. 20B, the bottom of the reaction cell 330 is designed to have a flat area so that plural measurement apparatuses 100, when put into the reaction cell 330, can be scattered at the bottom with no overlap. The external antennas are arranged in the plane beneath and parallel to the bottom of the reaction cell. In this case, a vibrator for applying mechanical vibration to the substrate, on which the external antennas are formed, is installed. FIG. 20A is a view showing the layout, in which the vibrator 342 is installed beneath the reaction cell while FIG. 20B is a view showing the layout, in which the vibrator 343 is installed in the same level as that of the bottom of the reaction cell. By applying vibration to the reaction cell, the measurement apparatuses 100 are not overlapped and their chip sides face the bottom of the reaction cell, ensuring stable communication between the external antennas and the measurement apparatuses.

By designing so that the element formation area, in which the sensor of the measurement apparatus 100, circuit, and antenna are formed, is square-shaped and the aspect ratio between the size of one side and the thickness of the area is 5 or more (for example, 500 μm×500 μm, thickness 100 μm or less), the probability of the sides of the chips facing the bottom of the reaction cell is significantly decreased.

Insertion of the vibrator mentioned above has another desirable effect, namely the reaction between the probes fixed on the measurement apparatuses and the targets is accelerated. Well stirring and increased molecular moving velocity achieved by applying vibration enables the reaction to end in a shorter time period.

(Embodiment 20)

The configuration of the measurement system according to an aspect of the present invention is described below. FIG. 21A is a view showing the appearance of the system while FIG. 21B is a view showing the configuration-of the agent disperser 347 in a shielded box 350, the reaction cell (microtiter plate) 360 containing the sample solution and the measurement apparatuses, and the integrated external antennas. To ensure the information communication and power transmission between the external control unit and the measurement apparatuses 100, an electromagnetic wave, a change in the magnetic field, or a change in the electric field is used. In this case, any measures must be taken to prevent the electromagnetic wave from diffusing into the surrounding area. To do so, a portion considered to be the source of electromagnetic wave diffusion is put in the shielded box. Since in this configuration, the electromagnetic wave does not leak into the surrounding system area, sufficient power is supplied from the external antennas to the measurement apparatuses 100 in the reaction cell to ensure such an intensity level of the electromagnetic wave, a change in the magnetic field, or a change in the electric field that stable communication may be established.

According to the embodiment of the present invention mentioned above, measurements can be conducted in a shorter time period using the small-sized measurement system and a small amount of sample. Namely, a simple and fast measurement system is available. In addition, the probes can be uniformly fixed on the measurement apparatuses and the probes appropriate for difference measurements may be easily selected. Plural target materials can be measured in a single reaction cell concurrently. The sensor information and the identification numbers of the measurement apparatuses can be sent/receive to/from the measurement apparatuses and the external control unit with no direct contact between them.

The present invention provides further characteristics described below.

(1) A biological and chemical sample measurement apparatus, wherein the substrate, on which the measurement apparatus is formed, surface-modified to fix a probe, a specific probe is fixed on the substrate, a sensor for detecting a target captured by the prove, is mounted, a mechanism for determining the presence or the amount of the captured targets and digitizing the measured values to transfer to an external unit by device of an electromagnetic wave, a change in the magnetic field, or a change in the electric field is assembled, and an identification number, by which the specific measurement apparatus and the probe type can be identified, is stored in the measurement apparatus.

(2) A biological and chemical sample measurement apparatus defined in (1), wherein the probe is any of antigen, antibody, nucleic acid, and any type of protein, which is detected as a target.

(3) A biological and chemical sample measurement apparatus, wherein a sensor for detecting temperature, pressure, ion concentration, or sugar is mounted on the measurement apparatus, a mechanism for digitizing the signals from the sensor to transfer to an external unit by device of an electromagnetic wave, a change in the magnetic field, or a change in the electric field is assembled, and an identification number, by which the specific measurement apparatus and the probe type can be identified, is stored in the measurement apparatus.

(4) A biological and chemical sample measurement apparatus defined in (1) or (3), wherein a function block, which sends/receives, detects, and controls sending/receiving an electromagnetic wave, a change in the magnetic field, or a change in the electric field for sensing, sensor signal processing, identification number recording, and signal transmission and information communication with the external unit, is assembled on the same semiconductor substrate.

(5) A biological and chemical sample measurement apparatus defined in (1) or (3), wherein an antenna for sending/receiving electromagnetic waves is formed on the same semiconductor substrate as the function block defined in (4) for controls sending/receiving an electromagnetic wave, a change in the magnetic field, or a change in the electric field for sensing, sensor signal processing, identification number recording, and signal transmission and information communication with the external unit and the distance between the two farthest points of the appearance of the measurement apparatus including the antenna is within 3.0 mm.

(6) A biological and chemical sample measurement apparatus defined in (1) or (3), wherein power, which is consumed by the function block defined in (4) for controls sending/receiving an electromagnetic wave, a change in the magnetic field, or a change in the electric field for sensing, sensor signal processing, identification number recording, and signal transmission and information communication with the external unit, is supplied externally according to an electromagnetic wave, a change in the magnetic field, or a change in the electric field and received by the antenna defined in (5).

(7) A biological and chemical sample measurement apparatus define in (1) or (3), wherein a semiconductor, glass, or ceramic substrate is used as a material for the substrate, on which the function block for each measurement apparatus defined in (4) is mounted.

(8) A biological and chemical sample measurement apparatus defined in (2), wherein an field effect transistor (hereafter, simply referred to as the FET) is mounted and the presence of specific coupling is determined by fixing the probe at the gate of the FET and detecting any change in conductivity between the source and drain of the transistor depending on coupling/decoupling between the probe and the target.

(9) A biological and chemical sample measurement apparatus, wherein the presence of the specific coupling is determined by inserting separate electrodes in a solution, fixing a probe on the electrode, observing for any change in impedance between the electrodes depending on coupling/decoupling between the probe and the target to identify the presence or the amount of the target captured.

(10) A biological and chemical sample measurement apparatus defined in (2), wherein when materials, which couple specifically to the probes, and molecules, which play a central role in the oxidization and reduction process and bind selectively only to specific coupling sites, are input, the sensor detects electrochemically the presence of the specific coupling and sends detected data to an external control unit as electric signals via an information communication device assembled on a chip.

(11) A biological and chemical sample measurement system defined in (2), comprising a photodiode as the sensor, the photodiode detecting the presence of the specific coupling.

(12) A biological and chemical sample measurement apparatus defined in (1) or (3), comprising a memory area for storing digitized measurement signals temporarily, from which the signal data is read out to transfer to the external unit.

(13) A biological and chemical sample measurement apparatus defined in (1) or (3), wherein analog signals measured by the sensor installed on the semiconductor device are digitized into numerical data by a comparator referencing a specific reference signal or an analog/digital converter, written into the memory area for temporary storage, and read out from the memory area for transfer to the external unit.

(14) A biological and chemical sample measurement kit using the biological and chemical sample measurement apparatus defined in (1) or (3), wherein the kit comprises the plural biological and chemical measurement apparatuses, the substrate is surface-modified to fix a probe, plural kinds of probes are fixed for each measurement apparatus, and an identification number, by which the specific measurement apparatus and the fixed probe type can be identified, is stored in the measurement apparatus.

(15) A biological and chemical sample measurement kit defined in (1), (3) and (14), wherein any of the measurement apparatuses, on which any antigen, antibody, nucleic acid, or any of protein is fixed as a probe, and any of the measurement apparatuses, on which a sensor for sensing temperature, pressure, ion concentration, or sugar is mounted, are integrated together.

(16) A system using a biological and chemical sample measurement, comprising plural biological and chemical sample measurement apparatuses and a reaction cell for putting the measurement apparatuses and samples, wherein the biological and chemical sample measurement apparatuses comprise specific probes, sensors, a device for information communication, and a device for recording identification numbers, by which probe types can be identified and have various kinds of probes fixed, the sensors detect electrically the presence of the specific coupling when a sample solution is input in the reaction cell, and the external control unit performs information communication with the measurement apparatuses by device of any of an electromagnetic wave, a change in the magnetic field, and a change in the electric field via the information communication device.

(17) A biological and chemical sample measurement system, wherein when the biological and chemical sample measurement apparatuses defined in (16) are put in a reaction cell containing biological or chemical samples, the targets are captured, capture signals are detected, and measurement signals are sent to an external control unit.

(18) A biological and chemical sample measurement system, wherein when the plural biological and chemical sample measurement apparatuses defined in (1) or (3) are put in a reaction cell containing biological or chemical samples, once a specific first identification number is sent from an external unit, the measurement apparatuses receive it and match against its identification number internally stored, and if matched, the sensor on the measurement apparatus, of which identification number matches the received one, sends the result of measurement to an external transmitter/receiver, the external transmitter/receiver sends a second identification number and the measurement apparatus with matched identification sends the result of measurement to the external transmitter/receiver, and this process is repeated.

(19) A biological and chemical sample measurement system, wherein when the plural biological and chemical sample measurement apparatuses defined in (1) or (3) are put in a reaction cell containing biological or chemical samples, an external control unit sends a signal for specifying a specific signal level, the measurement apparatuses receive this signal and match it against a signal level internally stored in the sensors on them, and if matched, the identification number with the signal level matched is sent to an external transmitter/receiver, alternately, if plural signal levels are detected, the external control unit sends the signals corresponding to different signal levels sequentially and the measurement apparatuses with sensor signals associated with these signal levels send their own identification numbers to transfer to the external control unit.

(20) A biological and chemical sample measurement system, wherein the measurement system communicates signals between the measurement apparatuses defined in (1) or (3) and an external control unit, the external control unit generates clock signals, and the bits of an identification number are sequentially sent on the transmission signals in synchronization with clock signals.

(21) A biological and chemical sample measurement system, comprising a reaction cell, in which are the biological and chemical sample measurement apparatuses defined in (1) or (3), and the external control unit, wherein antennas for sending/receiving between the measurement apparatuses and the external control unit are included in a same box as that of the measurement apparatuses and the box has an electromagnetic shielding function.

(22) A biological and chemical sample measurement system, wherein the electromagnetic shielding function of the box defined in (21) can attenuate electromagnetic wave emitted by antennas connected to the external control unit to 1/1000 or less outside of the box.

(23) A biological and chemical sample measurement system, wherein plural reaction cells, in which the biological and chemical sample measurement apparatuses defined in (1) or (3) are put and the system communicates information with the measurement apparatuses in the plural reaction cells via a same antenna connected to the external control unit or plural antennas corresponding to each reaction cell.

(24) A biological and chemical sample measurement system using a biological and chemical sample measurement kit defined in (15), comprising a temperature adjustment heater and a piezoelectric element or an ion concentration adjustment dispenser, and further comprising a device for monitoring any of temperature, pH, and ion concentration, at a regular interval by the biological and chemical sample measurement apparatuses defined in (3) input in the reaction cell and controlling the temperature adjustment heater and piezoelectric element or ion concentration adjustment dispenser to keep samples at optimal temperature or optimal ion concentration level.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A measurement system, comprising:
a plurality of chips, each of the plurality of chips including:
at least one probe for capturing biological materials,
a sensor connected to the at least one probe,
an information communication device,
an information storage device for storing recognition information specific to a corresponding chip of the plurality of chips, and
a clock signal generator for generating a clock for driving the sensor;
at least one reaction cell for containing a corresponding at least one of the plurality of chips; and
one external control unit having an antenna, said antenna for simultaneously sending a plurality of the recognition information to corresponding chips, and simultaneously receiving detection information obtained by each sensor on said corresonding chips,
Wherein the clock signal generator in each chip is driven when the external control unit simultaneously sends the recognition information to said corresponding chips, and the sensor in each chip is driven by the clock signal generator.

2. The measurement system defined in claim 1, wherein the plurality of chips have different kinds of probes, respectively, and different kinds of recognition information, respectively.

3. The measurement system of claim 1, wherein the sensor is configured to detect a specific coupling via electricity, the specific coupling being a coupling between a probe and a material specifically bound to a probe.

4. The measurement system of claim 3, wherein the sensor has a field effect transistor, and wherein a probe is fixed on the surface of the transistor to detect the specific coupling via electricity based on any change in conductivity of the transistor.

5. The measurement system of claim 3, wherein the sensor has at least an electrode, wherein a probe is fixed on a surface of the electrode, and wherein the electrode is configured to detect the specific coupling via electricity based on any change in impedance.

6. The measurement system of claim 3, wherein the sensor has at least an electrode, wherein a probe is fixed on a surface of the electrode, and wherein the electrode is configured to detect the specific coupling via electricity based on any change in current on the electrode caused by an electrochemical reaction arising from the specific coupling.

7. The measurement system of claim 3, wherein the sensor has at least a photodiode, wherein a probe is fixed on a surface of the photodiode, and wherein the photodiode is configured to detect the specific coupling via electricity by capturing light emitted from an illuminant reaction.

8. The measurement system of claim 1, wherein each of the plurality of chips comprises a silicon substrate.

9. The measurement system of claim 1, wherein the sensor is configured to detect a specific coupling via electricity, the specific coupling being a coupling between a probe and a material specifically bound to the probe, and the information communication device further sends the recognition information to the external control unit as an electrical signal.

10. A measurement system, comprising:
a reaction cell, comprising:
probes for capturing biological materials; and
a plurality of chips, each of the plurality of chips including:
a sensor for detecting the biological materials captured by at least one of the probes,
an information communication device,
an information storage device storing recognition information specific to a corresponding chip of the plurality of chips, and
a clock signal generator for generating a clock for driving the sensor; and
one external control unit having an antenna, said control unit for simultaneously sending a plurality of the recognition information to corresponding chips, and simultaneously receiving detection information obtained by each sensor on said corresponding chips,
wherein the clock signal generator in each chip is driven when the external control unit simultaneously sends the recognition information to said corresponding chips, and wherein the sensor in each corresponding chip is driven by the clock signal generator.

11. The measurement system of claim 10, wherein each of the plurality of chips comprises a silicon substrate.

12. The measurement system of claim 10, wherein the sensor is configured to detect a specific coupling via electricity, the specific coupling being a coupling between the probe and a material specifically bound to the probe.

13. The measurement system of claim 10, wherein the sensor is configured to detect a specific coupling via electricity, the specific coupling being a coupling between the probe and a material specifically bound to the probe, and the information communication device sends the detection information and the recognition information to the external control unit as an electrical signal.

14. The measurement system of claim 1, wherein each of the plurality of chips further comprises a matching circuit for matching the recognition information stored in the information storage device to the recognition information sent by the external control unit.

15. The measurement system of claim 10, wherein each of the plurality of chips further comprises a matching circuit for matching the recognition information stored in the information storage device to the recognition information sent by the external control unit.

16. The measurement system of claim 1, wherein the external control unit is configured to send a specific level of signals and the chip containing the detection information corresponding to the signal level is configured to reply to the external control unit.

17. The measurement system of claim 10, wherein the external control unit is configured to a send specific level of signals and the chip containing the detection information corresponding to the signal level is configured to reply to the external control unit.

* * * * *

SEQUENCE LISTING

<160> NUMBER OF SEQ ID NOS: 6

<210> SEQ ID NO 1
<211> LENGTH: 29
<212> TYPE: DNA
<213> ORGANISM: Artificial Sequence
<220> FEATURE:
<223> OTHER INFORMATION: DNA primer

<400> SEQUENCE: 1
caggacaggc acaaacacgc acctcaaag                        29

<210> SEQ ID NO 2
<211> LENGTH: 52
<212> TYPE: DNA
<213> ORGANISM: Artificial Sequence
<220> FEATURE:
<223> OTHER INFORMATION: DNA primer

```
<400> SEQUENCE: 2
aacagctttg aggtgcgtgt ttgtgcctgt cctggggaga gaccggcgca ca           52

<210> SEQ ID NO 3
<211> LENGTH: 95
<212> TYPE: DNA
<213> ORGANISM: Artificial Sequence
<220> FEATURE:
<223> OTHER INFORMATION: DNA primer supplied from Amersham
                        Pharmacia Biotech

<400> SEQUENCE: 3
ctttcttgcg gagattctct tcctctgtgc gccggtctct cccaggacag gcacaaacac   60
gcacctcaaa gctgttccgt cccagtagat tacca                              95

<210> SEQ ID NO 4
<211> LENGTH: 95
<212> TYPE: DNA
<213> ORGANISM: Artificial Sequence
<220> FEATURE:
<223> OTHER INFORMATION: DNA primer supplied from Amersham
                        Pharmacia Biotech

<400> SEQUENCE: 4
ctttcttgcg gagattctct tcctctgtgc gccggtctct cccaggacag gcactaacac   60
gcacctcaaa gctgttccgt cccagtagat tacca                              95

<210> SEQ ID NO 5
<211> LENGTH: 22
<212> TYPE: DNA
<213> ORGANISM: Artificial Sequence
<220> FEATURE:
<223> OTHER INFORMATION: DNA primer supplied from Amersham
                        Pharmacia Biotech

<400> SEQUENCE: 5
aacagatttg aggtgcgtga tt                                            22

<210> SEQ ID NO 6
<211> LENGTH: 22
<212> TYPE: DNA
<213> ORGANISM: Artificial Sequence
<220> FEATURE:
<223> OTHER INFORMATION: DNA primer supplied from Amersham
                        Pharmacia Biotech

<400> SEQUENCE: 6
aacagctttg aggtgcgtga ta                                            22
```